(12) United States Patent
Sorrell et al.

(10) Patent No.: US 6,497,875 B1
(45) Date of Patent: Dec. 24, 2002

(54) MULTILAYER SKIN OR DERMAL EQUIVALENT HAVING A LAYER CONTAINING MESENCHYMAL STEM CELLS

(75) Inventors: J. Michael Sorrell; Arnold I. Caplan, both of Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/171,445

(22) PCT Filed: Apr. 24, 1997

(86) PCT No.: PCT/US97/06760

§ 371 (c)(1),
(2), (4) Date: Oct. 26, 1998

(87) PCT Pub. No.: WO97/41208

PCT Pub. Date: Nov. 6, 1997

Related U.S. Application Data

(60) Provisional application No. 60/016,317, filed on Apr. 26, 1996.

(51) Int. Cl.$^7$ ............................. C12N 5/06; C12N 5/08; C12N 11/00; C12N 11/02
(52) U.S. Cl. ..................... 424/93.7; 435/1.1; 435/174; 435/177; 435/325; 435/366; 435/395
(58) Field of Search .................. 424/93.7; 435/174, 435/325, 395, 366, 177, 1.1

(56) References Cited

U.S. PATENT DOCUMENTS

| | | | |
|---|---|---|---|
| 4,505,266 A | 3/1985 | Yannas et al. | 128/898 |
| 5,354,736 A | 10/1994 | Bhatnagar | 514/14 |
| 5,709,854 A | * 1/1998 | Griffith-Cima et al. | 424/93.7 |
| 5,800,811 A | 9/1998 | Hall | 424/93.7 |

OTHER PUBLICATIONS

Krejci, et al., "In Vitro Reconstitution of Skin: Fibroblasts Facilitate Keratinocyte Growth and Differentiation of Acellular Reticular Dermis," *The Journal of Investigative Dermatology*, 97(5):843–848 (1991).

Livesey, et al., "Transplanted Acellular Allograft Dermal Matrix," *Transplantation*, 60(1):1–9 (1995).

* cited by examiner

*Primary Examiner*—David M. Naff
(74) *Attorney, Agent, or Firm*—Elliot M. Olstein; Raymond J. Lillie

(57) ABSTRACT

A multilayer skin equivalent is formed having a scaffold layer containing dermis-forming cells, and a keratinocyte layer. The dermis-forming cells and keratinocytes are preferably autologous, and the dermis-forming cells can be human mesenchymal stem cells (MSCs), dermal fibroblasts (e.g., papillary or reticular dermal fibroblasts) or mixtures thereof. The scaffold is preferably type I collagen alone, or types I and II collagen in combination. Also formed is a multilayer skin equivalent having a scaffold layer containing a layer of extracellular matrix component containing papillary dermal fibroblasts in laminar relationship with a layer of extracellular matrix component containing reticular dermal fibroblasts, and a keratinocyte layer. A multilayer dermal equivalent is provided having a layer of extracellular matrix component containing papillary dermis-forming cells and a layer of extracellular matrix component containing reticular dermis-forming cells. In another embodiment, the dermal equivalent has a layer containing MSCs and a layer selected from a layer of extracellular matrix component containing papillary dermis-forming cells and a layer of extracellular matrix component containing reticular dermis-forming cells, and optionally a keratinocyte layer. In the skin and dermal equivalents, at least one layer may contain an agent that promotes adhesion or angiogenesis. Also present may be a bioactive agent that enhances proliferation, commitment or differentiation of mesenchymal stem cells into dermal components, either in vitro or in vivo. An injectionable composition is also provided containing dermis-forming cells and an extracellular matrix component in a pharmaceutically acceptable injectable carrier.

18 Claims, 5 Drawing Sheets

FIG. IA
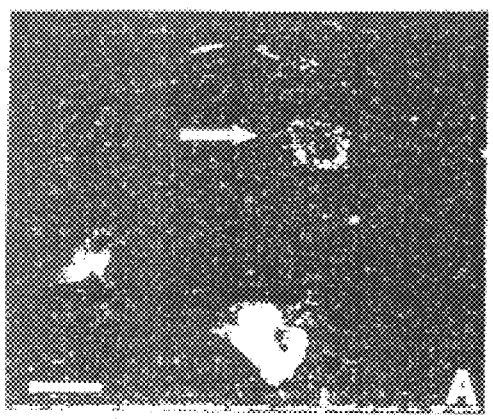
FIG. IB
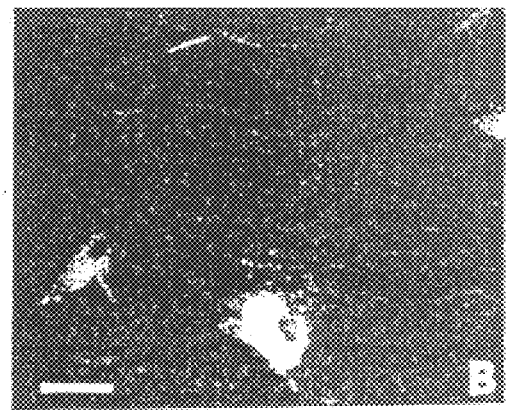
FIG. 5A
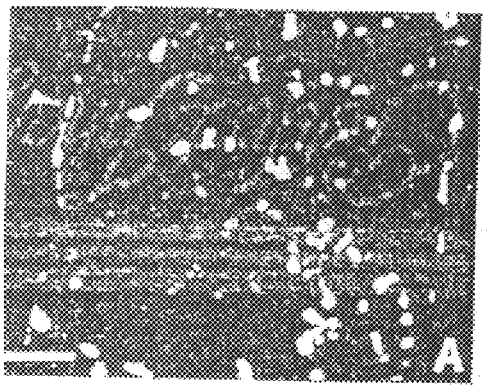
FIG. 5B
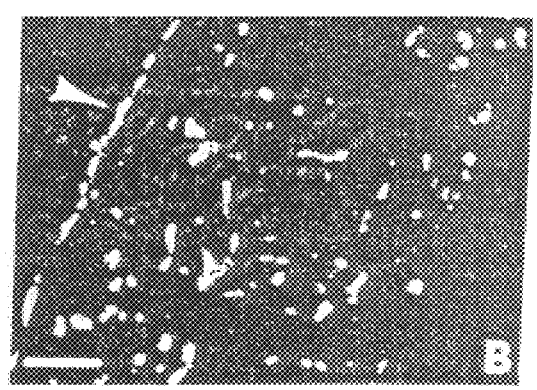

MULTILAYER SKIN OR DERMAL EQUIVALENT HAVING A LAYER CONTAINING MESENCHYMAL STEM CELLS

This application claims the benefit of provisional application 60/016,317 filed on Apr. 26, 1996.

BACKGROUND OF THE INVENTION

Adult skin consists of an epidermis generated principally by keratinocytes [1] and a complex dermis, populated by fibroblastic cells of mesenchymal origin [2] interspersed with vasculature, hair follicles, and other accessory structures. Within the dermis are histologically distinct regions: the papillary dermal layer just below the epidermal basement membrane, and the reticular dermal layer extending deeper to the hypodermal areas containing muscle and fat. There is no formal lineage map for dermal fibroblasts. Although types of dermal cells in culture have been described by elaborate morphological and biochemical criteria [3] the lineage progression from a mesenchymal dermal progenitor cell to reticular, papillary and follicular dermal cells is not understood.

Among the dermal fibroblasts appear to be a restricted population of mesenchymal stem cells (MSCs) [4] first identified as pluripotent, adherent cells of the bone marrow stroma [5]. MSCs in the adult are cells capable of giving use to a variety of mesenchymal phenotypes, including bone, cartilage, muscle, tendon, ligament, adipocytes, connective tissues, and dermis. Fleming et al. [4]) at Case Western Reserve University, have demonstrated that a small subpopulation of the fibroblastic cells residing in the dermis react with monoclonal antibody SH2, a reagent that specifically labels MSCs in bone marrow [6]. The MSCs are clustered near vasculature, hair follicles, and adjacent to the epidermal basement membrane, although the significance of this pattern of localization has not yet been determined. Interestingly, Fleming and coworkers [4] also suggest that the number of MSCs in dermis, based on SH2 reactivity, decreases with the age of the patient to undetectable levels after age 20. This observation may contribute to our understanding of skin aging and its potential for self-renewal.

Relatively little is known about the embryologic development of human skin, although Holbrook and coworkers [2,7]have described a sequence of layer appearance with focus on the vasculature and appendage elements. Markers for extracellular matrix molecules, cell surface proteins, and growth factors have been used to help characterize the layers of skin during development, but the lack of model systems for in vitro differentiation has hampered progress in the field. Skin organ cultures [7] or embryonic side spheroids are the best system reported to study embryonic s development. These cultures consist of patches of full-thickness side introduced into suspension culture, where they round up to form spherical bodies. These cultures have epidermis on the outside and dermis on the inside, and they progress through a relatively normal sequence of developmental events. Because of the geometry of these bodies, it is difficult to use the spheroids to establish unequivocally the lineage progression of dermal cells.

In recent years, living skin equivalents [1] have been established, and the technology for reconstituting the epidermal layer from autologous or allogeneic keratinocytes has become highly advanced. The feeder layers for these keratinocyte cultures are generally fibroblasts in a formulation suitable for co-culture. While these skin equivalents can function in grafts, the fibroblastic feeder layers are not the same as a true, multi-layered dermis.

The principal needs for skin repair and regeneration methods and products are severe burns and skin ulcers. While there is substantial demand for improved therapy, there are no completely satisfactory products either on the market or in clinical development. The scope of the need in the United States is estimated as follows:

| Type of injury | Estimated U.S. patient population |
| --- | --- |
| Partial thickness burns | 2,000,000 |
| Hospitalized burn patients | 100,000 |
| Burns requiring skin grafts | 70,000 |
| Skin grafts performed (reflects multiple sites per patient) | 150,000 |
| Pressure (decubitus) ulcers | 1,500,000 |
| Venous ulcers | 500,000 |
| Diabetic ulcers | 600,000 |
| Moh's surgical wounds | 100,000 |

Partial thickness burns constitute those where the burn involves the surface layer of skin (epidermal layer) and into, but not through the underlying dermal layer. Most of these injuries are treated without graft or other tissue replacement. This conservative approach is effective because keratinocytes (the primary cell type of the epidermis layer) required to repair the epidermal layer are present in the dermis, particularly in the tissue surrounding hair follicles and sebaceous glands.

Patients with more extensive burns generally can not be adequately treated through spontaneous healing because (1) these burns frequently destroy the underlying dermal layer which provides the source of keratinocytes, (2) healing for full thickness wounds must occur from the margins, which is a long process that exposes the patient to a high risk of infection through unprotected tissue and (3) spontaneous healing will lead to serious scar-ring and skin contraction that is both cosmetically unattractive and may be physically restrictive due to loss of flexibility and range of motion.

Severe burns are a primary application for mesenchymal stem cell therapy because they represent a serious medical threat, they result In a high cost of treatment, and they require a long recovery period. Serious burns are frequently referred to hospitals with specialized burn units or for serious cases, the major burn centers.

Decubitus (pressure) ulcers are one of the continuing problems associated with treatment in nursing homes and hospitals dealing with bed-ridden patients. They occur due to localized pressure that restricts blood circulation to the skin. The ulcers may be quite large in area and penetrate to the full thickness of the dermal layer. They are difficult to heal and require substantial nursing resources.

Venous ulcers result from poor circulation, particularly in the legs, associated with aging. Age-deteriorated veins can lose the "valve" function which keeps blood moving towards the heart. When this occurs, there is pooling of blood in the extremities and ineffective removal of toxins. This results in deterioration of the skin cells fed by the affected blood vessels.

Diabetic ulcers occur through an analogous process. Diabetes causes deterioration of the arteries through accumulation of advanced glycosylation end products (excess sugar that binds to proteins) and possibly sorbitol. As these arteries deteriorate they are unable to supply skin cells adequately, leading to cell death. As in the case of venous stasis, there is an underlying circulatory defect that requires correcting to gain fill healing. However, even if the defect is corrected, the s ulcers may persist unless properly treated.

A skin replacement is the ideal product for treating dermal ulcers. Repeated applications may be needed because the underlying defects are frequently not curable and the ulcers recur in 20–50% of cases, Surgical wounds associated with the excision of skin cancers represent another major application for mesenchymal stem cell skin regeneration. Surgical wounds are frequently deep and cosmetically disfiguring. Treatment to accelerate healing and minimize scarring (there is a disproportionate incidence of skin cancers lesions on the face and neck) represents a significant need.

There are limited numbers of skin replacement products currently on the market and none of those in development appear likely to fully meet clinical needs, especially for full- and partial-thickness products. The measures of clinical success in skin replacement include (1) the ability to treat a wide range of dermal injuries; (2) the ability to replace or regenerate both the epidermis and the dermis skin layers: (3) a high degree of "take" or acceptance and growth by the underlying tissue; (4) shortening of the natural healing process; and (5) minimal scarring.

There is little evidence that current products shorten the time to healing. Therefore, the potential exists to substantially expand the market with a therapeutic approach that both improves clinical outcomes and accelerates recovery.

True multilayer skin equivalents have not been previously possible as existing skin equivalents use a "surrogate matrix" for keratinocytes, such as processed allograft tissue or autograft skin, and all such surrogates lack a complete tissue morphogenic capacity.

Further, the very serious negative which compromises the attractiveness of dermal replacement using autograft from harvested skin is the need to create a substantial surgical injury that requires a long recovery period, exposes the patient to increased risk of infection through further disruption of the dermal barrier and is exceedingly painful.

SUMMARY OF THE INVENTION

The use of mesenchymal stem cells (MSCs) enables, for the first time, the development of an autologous dermal regeneration product. The skin repair products of the invention provide a true, morphogenic. multilayer, skin equivalent involving autologous MSC-derived dermoblasts and cultured human keratinocvtes thus comprising an autologous or autologous and allogeneic cell combination product. They provide full thickness dermal regeneration, producing accelerated healing and reduced scarring in a non-allergenic format.

In one aspect the invention provides a multilayer skin equivalent having (i) a scaffold layer incorporated with dermis forming cells, and (ii) a keratinocyte layer. The dermis-forming cells are preferably autologous and can be human mesenchymal stem cells, dermal fibroblasts (e.g., papillary or reticular dermal fibroblasts) or mixtures thereof. The scaffold is preferably type I collagen alone or type I and type III collagen in combination. It is also preferred that the dermis-forming cells be derived from the individual to be treated with the multilayer skin equivalent. Preferably, the keratinocytes are also autologous.

In another aspect, the invention provides a multilayer dermal equivalent comprising at least one dermis-forming layer selected from the group consisting of (i) a layer of at least one skin-associated extracellular matrix component containing papillary dermal fibroblasts; and (ii) a second layer of at least one skin-associated extracellular matrix component containing reticular dermal fibroblasts. Preferred embodiments of this aspect include those where the scaffold or dermis-forming layer is a multilayer selected from the group consisting of (a) a layer containing isolated papillary dermis-forming cells and a layer containing isolated reticular dermis-forming cells; (b) a layer containing isolated papillary dermis-forming cells and a layer containing isolated, culture expanded mesenchymal stem cells; and (c) a layer containing isolated reticular dermis-forming cells and a layer containing isolated, culture expanded mesenchymal stem cells. The papillary and reticular fibroblasts are preferably from the same individual, and this is preferably the individual to whom the multilayer dermal equivalent is to be administered.

In embodiments which comprise a layer of skin-associated extracellular matrix components containing papillary dermal fibroblasts in laminar relationship with a layer containing isolated mesenchymal stem cells, the product is positioned at-site on the recipient with the layer containing the mesenchymal stem cells in contact with the underlying tissue. In embodiments which comprise a layer of skin-associated extracellular matrix components containing reticular dermal fibroblasts in laminar, relationship with a layer containing isolated mesenchymal stem cells the product is positioned at-site on the recipient with the layer containing the reticular fibroblasts in contact with the underlying tissue.

In yet another aspect the invention provides a multilayer skin equivalent having (i) a scaffold layer comprising a first layer of at least one skin-associated extracellular matrix component containing papillary dermal fibroblasts and, in laminar relationship therewith, a second layer of at least one skin-associated extracellular matrix component containing reticular dermal fibroblasts; and (ii) a keratinocyte layer. The particular preferred embodiments of the dermis-forming layer are the same as those described above.

In a further aspect the invention provides an injectable composition comprising an injectable composition comprising dermis forming cells and at least one skin-associated extracellular matrix component in a pharmaceutically acceptable injectable carrier. The dermis forming cells can be isolated, culture-expanded mesenchymal stem cells, dermal fibroblasts and combinations thereof. They are preferably human and most preferably autologous. The dermal fibroblasts can be papillary dermal fibroblasts, reticular dermal fibroblasts or combinations thereof. The composition can further include keratinocytes.

Permutations of those aspects and embodiments which include the presence of MSCs with keratinocytes and/or committed or differentiated dermoblasts are those in which the various cell types can be combined ex vivo during the manufacture of the product or one or more of such cell types can be administered to the recipient of the dermal or skin equivalent product either by adding such cells to the product while in position on an area of skin to be repaired or, alternatively, can be administered in vivo systemically or locally.

With the decline in the presence of hMSCs, comes a significant decrease in of the ability of skin to regenerate the dermal layer. Our objective is to re-establish the ability of the patient to regenerate skin by providing a scaffold rich in culture expanded autologous hMSCs in contact with the wound bed. Our approach provides the ability to reproduce the normal multi-layered architecture of the skin and the normal physiology of skin turnover. The presence of an abundance of dermal progenitor cells will eliminate the need for subsequent regrafts and since the material will be entirely cells of non-foreign origin, there will be no risk of rejection or immune response.

The hMSC cell therapy of the present invention provides the first in vivo skin progenitor product for wound care. and thus is the first true dermal regeneration product. Human MSC dermal progenitors can be injected directly into the wound or ulcer site, formed into dermal skin equivalents in a scaffold or combined with keratinocytes to create the first functional multi-layer skin equivalents.

Unlike the use of non-immunologic fibroblasts or cadaveric tissue, autologous hMSCs would form new dermis under the control of local bioactive factors (or added bioactive factors) without harvesting patient autografts or rejection from allograft tissue. Under these circumstances, autologous hMSC products replicate the therapeutic success of skin autografts, accelerate healing, reduce the need to harvest patient dermis, and substantially reduce hospitalization time and cost.

The skin and dermal regeneration and equivalent products of the invention include skin-associated extracellular matrix components, such as collagen (preferably type I or type I in combination with type III), modified collagen, and/or elastin, ICAMs, NCAM, laminin, fibronectin, proteoglycans (HSPG, CSPG), tenascin, heparin binding growth factors, E-cadherin and/or fibrillin, in combination with isolated, culture-expanded mesenchymal stem cells (hMSCs). These mesenchymal stem cells are the naturally occurring progenitors which give rise to multiple structural and connective tissues, including normal dermis. Unlike skin equivalents produced from collagen substrates alone or produced with a layer of non-specific fibroblasts, the dermal regeneration product of the invention has significantly more dermal regeneration potential to reconstitute the patient's own dermis which has degenerated through burns, ulcerations, or interrupted through acute injury or surgery. The ability to reconstitute normal dermis is due to the inclusion of purified autologous dermal progenitor cells in the multilayer skin equivalent or other product configuration where regenerating a dermal component would be clinically beneficial.

The skin and dermal regeneration and equivalent products of the invention can further include a bioactive factor which enhances proliferation, commitment or differentiation of mesenchymal stem cells into dermal components, either in vitro or in vivo. Also, the products of the invention can further include at least one pharmaceutical agent which promotes adhesion or angiogenesis of the dermal skin equivalent.

In order to obtain mesenchymal stem cells, it is necessary to isolate rare pluripotent mesenchymal stem cells from other cells in the bone marrow or other MSC source. Typically, a 10–20 cc aspirate is harvested from a patient which yields 1,000–5,000 hMSCs. Approximately 1–5 million culture-expanded autologous hMSCs are then returned in the form of a skin equivalent, which is applied as a skin patch or wound cover. The marrow or isolated mesenchymal stem cells can be autologous, allogeneic or from xenogeneic sources, and can be embryonic or from post-natal sources. The use of autologous cells is preferred. Bone marrow cells may be obtained from iliac crest, femora, tibiae, spine, rib or other medullary spaces. Other sources of human mesenchymal stem cells include embryonic yolk sac, placenta, umbilical cord, periosteum, fetal and adolescent skin, other soft tissues and blood.

The skin equivalents of the invention are indicated for use in regenerating dermis which has been lost through burn, ulceration, abrasion, laceration injury, or surgical wound. They are also suitable for treating patients who present with partial to full thickness burns, various dermal-involved ulcerations, and for regenerating tissue during plastic or reconstructive surgery. These skin equivalents contain autologous hMSCs, are dermagenic and, as such, regenerate dermis directly at the graft site where they are able to differentiate into one or more of the dermis-forming papillary, papillary follicular and reticular dermal cells. This process is known as Regenerative Dermal Tissue Therapy.

The direct dermagenic activity of hMSCs is superior to harvesting skin autografts or other dermal collagen scaffolds because hMSCs are able to recapitulate the original morphogenic (tissue-forming) events involved in dermal development. Harvested autografts or collagen substrates are not able to recruit sufficient newly formed dermal cells, which have differentiated from mesenchymal progenitor cells (hMSCs), from surrounding tissue or to accomplish this task in a suitable time period.

BRIEF DESCRIPTION OF THE DRAWINGS

FIGS. 1A and 1B. Papillary dermal cells labelled with DiI and reticular dermal cells labelled with DiO were plated together. The DiO-labelled cell (arrow) is visible when viewed with the fluorescein filter in place (A), but is not visible with the rhodamine filter in place (B). The DiI-labelied cells are visible with both filters. Magnification, 380×; 1 cm=26 µm.

FIGS. 5A and 5B. DiI-labelled papillary dermal cells (A) and reticular dermal cells (B) were seeded separately into type I collagen gels which were cultured for 14 days. Cross-sections of labelled gels reveal that both types of dermal cells are present within the interior of the gel and some cells have traveled to the gel surfaces (arrowheads). Magnification, 155×; 1 cm=65 µm.

DETAILED DESCRIPTION OF THE INVENTION

Figure 2A:
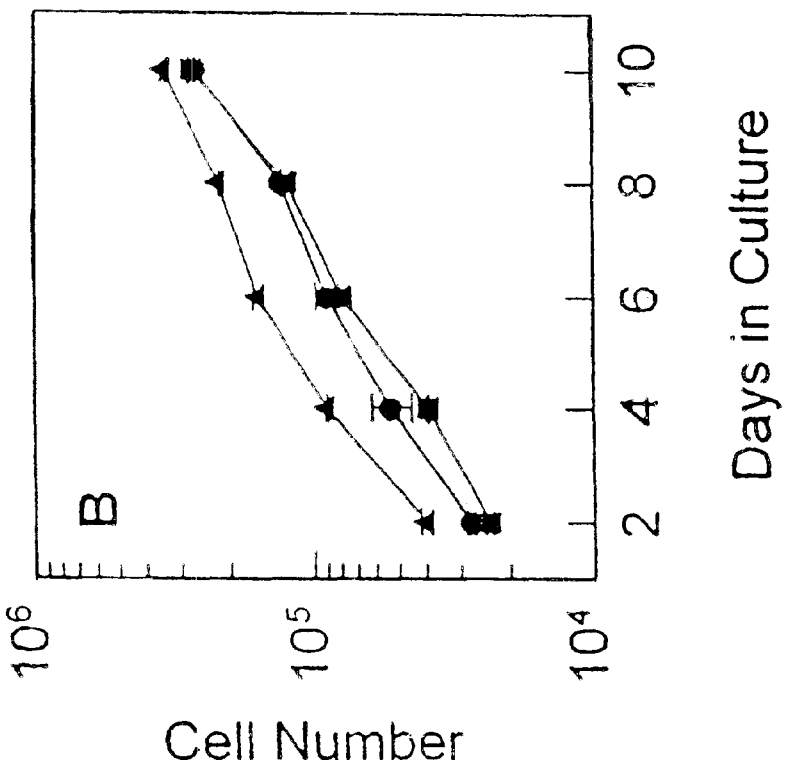
FIGS. 2A and 2B. Growth curves comparing papillary dermal fibroblasts (A) with reticular dermal fibroblasts (B) from the same individual were established using unlabelled cells (●), DiI-labelled cells (▲). and DiO-labelled cells (■), ± standard deviation of the mean.

Bilayer and muitilayer skin equivalents generally rely on dermal-forming cells to migrate into the matrix bed or framework of the replacement skin. This approach is referred to as "dermaconductive" in that the replacement skin matrix provides a scaffold upon which local dermal cells can migrate into the replacement skin matrix, form a new dermal layer while the skin replacement matrix resorbs. This is a passive process which requires extensive patient care, prolongs the healing process. and leaves the patient susceptible to infection at the wound site.

In contrast, the approach of the present invention is referred to as "dermagenic" in that the patient's own dermal forming cells are incorporated directly into the collagen scaffold of the skin equivalent. By increasing the number of the patient's own dermal progenitor cells (hMSCs) and incorporating them directly into the skin equivalent of the invention (together with an auto- or allograft keratinocyte layer), a normal and fully-functional multilayer skin can be restored using the body's own natural repair mechanism.

The skin equivalents of the invention comprise the only approach to regenerating normal dermal and epidermal skin layers without the need for painful patient autografts of normal tissue or for multiple replacement of synthetic or patient epidermal layers. They provide a one-time replacement and regeneration product.

Mesenchymal stem cells regenerate new dermis which conforms to the shape of the wound site. New dermis forms which is fully integrated with the surrounding normal host tissue. The collagen biomatrix components are eventually resorbed. Because the density of dermal-forming units is constant in the skin equivalent, the same overall rate of new dermal tissue forms regardless of the skin equivalent size. Substantial new full-thickness skin is formed 8–10 weeks after implantation. while the epidermal and dermal remodeling process is already well underway. Thereafter, significant tissue morphogenesis has taken place, only traces of the Dermagen biomatrix remain, and the neotissue is well integrated into the surrounding host tissue.

Recapitulating the events of original dermal tissue formation in the implant remodeling process ensures long-term structural integrity at the previous wound site. Only by starting with dermal progenitor cells can the formation of new dermal cellular components and nominal architecture of extracellular matrix molecules be formed.

The skin equivalent contains preferably hMSCs (culture-expanded autologous). Some versions also contain culture-expanded autologous or allogeneic epidermal cells which are sterile processed using FDA-approved manufacturing protocols. The hMSCs are incorporated into sterile patches (fresh or frozen) with or without the inclusion of culture-expanded keratinocytes for subsequent explantation.

Several embodiments are contemplated, designed to address defect situations ranging in both size and cellular composition, and include the following: (1) hMSCs in a collagen gel matrix, (2) hMSCs in a collagen gel matrix plus culture-expanded dermal cells in matrix, (3) hMSCs in a collagen gel matrix plus culture-expanded keratinocytes in matrix and (4) hMSCs in suspension for direct injection into wound bed, autograft, or other skin equivalent.

The skin equivalents are prepared using a scaffold material and the patient's own cells (hMSCs) which have been previously harvested for purification and expansion. Approximately 3–4 weeks after harvest, the patient's cells are used to commence the regenerative tissue therapy process.

Using sterile products, a bone marrow aspirate from the medial posterior iliac crest is obtained by standard aseptic technique at the patient's bedside or in an office procedure. A minimum sample size of 10–20 cc is required to assure an adequate concentration of hMSCs in the primary cultures. This can be obtained through enrichment of bone marrow, initiation of proliferation in vitro or by culture-expansion.

Since hMSCs decline with age, it is important to obtain the proper starting stem cell concentration. Nucleated cells are harvested from the bone marrow and subsequently processed in individual batches under sterile tissue culture conditions which promote selective attachment of patient's rare mesenchymal stem cells. Typically, only 100 to 500 hMSCs per 10–50 million nucleated marrow cells (or fewer in the case of elderly patients) attach and grow in tissue culture. This translates up to approximately,5,000 hMSCs per lOcc marrow aspirate. The remainder of the cell population contains various types of non-adherent hematopoietic cells, stromal cells and other adherent non-MSC cells, which are removed early in the cell culturing procedure.

Adherent marrow-derived hMSCs have homogeneous morphology, almost all being fibroblastic, with rare, polygonal cells. The adherent cells are seen as individual cells or small colonies of only a few cells on day 3; however, they replicate rapidly and form colonies of 50–200 cells within the first week of culture. By 10–14 days, the colonies of mesenchymal stem cells have expanded in size with each colony containing several hundred to several thousand cells.

To maintain mesenchymal stem cells in their undifferentiated state and to control their rate of replication, each primary hMSC culture is passaged into new culture vessels when the culture becomes ~80–90% confluent. Cells in newly passaged cultures attach to form a uniformly distributed layer of cells which are 25–35% confluent at the time they are passaged.

Cells continue to divide and are again passaged when cell density reaches ~80–90% confluence, yielding an average of 5 million cells per T-flask culture vessel. All preparations are culture-expanded in a fetal calf serum or chemically-defined medium which does not require the addition of fetal calf serum or other serum supplements. One such chemically-defined medium is described in commonly assigned, copending U.S. Ser. No. 08/464,599 filed Jun. 5, 1995.

Cells from each culture vessel can be repeated many times without a loss in the osteochondrogenic potential of the cells. Therefore, a single primary culture starting with 100 to 500 adherent human mesenchymal stem cells can be expanded to well over one billion ($1 \times 10^9$) cells. Typically, however, a small 10–20 cc marrow aspirate provides 25 primary culture vessels of up to 5 million cells, and consequently, sufficient cells for most skin equivalents of the invention can be obtained in 1–2 passages.

All procedures should be performed under standard aseptic conditions following accepted guidelines for therapeutic wound management procedures. Autologous mesenchymal stem cells will be maintained in a liquid suspension inside a sterile, sealed packet and should be maintained between 2° C. and 8° C. (36° F. and 46° F.) until the time of the dermal regeneration procedure, or thawed for 2 hours prior to explanation. All aspects of the patient's autologous hMSC procedure should be performed in accordance with the accepted standards for burn autograft and wound/laceration management.

Human mesenchymal stem cells (hMSCs) are used as the active, therapeutic component of products in three areas. First, MSCs are produced as part of a cellular support system for the epidermal keratinocyte layer in vitro during the production of a living skin equivalent product. Second, MSCs are used as part of a multi-layered skin equivalent graft in vivo serving as an active, dermagenic component to aid in the tissue regeneration process. Third, MSCs are used in deep wounds to regenerate parts of the reticular dermal layer and, potentially, to contribute to the regeneration. of muscle tissue in the hypodermal layer.

The invention provides products for effective regeneration therapy to create a third generation, multilayer, morphogenic skin equivalent, taking advantage of the dermal lineage potential of the MSC(s). An important component is the development of dermal fibroblasts in vitro starting from cultures of MSCs. Learning to recognize the markers of specific types of dermal fibroblasts and controlling the process of MSC differentiation permits better outcomes and outcome measurements in dermal regeneration. The MSCs and their progeny are designed to provide an active, regenerative dermal bed for the support of skin equivalent grafts. By replenishing parts of the papillary dermis, reticular dermis, and, possibly, muscle layers underneath the skin graft, a much more comprehensive remedy can be achieved.

One dermal regeneration product embodiment comprises autologous MSCs integrated as part of a multilayer, living skin equivalent. Another embodiment includes gel or other formulations of MSCs for implantation in deep wounds prior to placement of the living skin equivalent graft. The replacement of dermal layers of tissue offers an important opportunity to provide dermal growth factors that promote the proper and rapid integration of skin or skin equivalent grafts at a wound or ulcer site. Further, the reconstituted dermis becomes a cellular network to recruit new host vasculature quickly to support healing.

MSCs occur in both the papillary and reticular dermal layers of skin, and that the numbers of MSCs in dermis decrease with age, generally disappearing beyond 20 years of age. MSCs can undergo differentiation into dermal cells in multiple culture systems in vitro, including embryonic skin spheroids (ESS) and collagen gel layers. MSCs support keratinocyte growth in culture equally well as do dermal fibroblasts. Further, it is important to identify markers that can be used in vitro and in vivo to determine: (1) when the MSC has committed and/or differentiated to dermal fibroblasts and (2) what kind of dermal cell has been produced by the MSC. Presently, functional assays for dermal cells include the support of keratinocytes and the rate of shrinking of collagen gels. Immunochemical markers on the cells themselves or in the extracellular matrix are currently used, including collagens (I, III, IV, VI, VII), I-CAMS, N-CAM, laminin, fibronectin, proteoglycans (HSPG, CSPG), tenascin, E-cadherin, heparin-binding growth factor, and fibrillin, among others.

MSCs contribute more to the wound healing process than just dermal regeneration. When placed subcutaneously, MSC-based implants develop extensive host vasculature within a matter of days. Further, MSCs differentiate into various cell types in vitro, including fibroblastic cells that secrete a number of hematopoietic growth factors (e.g. GM-CSF, G-CSF, IL-6, IL-11) in response to external stimuli (e.g. IL-1). These observations suggest that MSCs may be effective tools to support the healing process by recruiting vasculature and supporting hematopoietic cells, in addition to forming structural components of the underlying dermis. In addition, MSCs have been shown to differentiate into muscle in cell culture and to differentiate and incorporate into myotubes in rodents in Wvo. Skeletal muscle is a mesenchymal tissue that lies in the hypodermal layer, and MSCs migrating out of a dermal implant afford some restoration potential to the muscle underlying a deep wound site. Thus, the presence of MSCs have multiple benefits at the wound site.

The dermal fibroblasts that make up the deep layers of skin are mesenchymal in origin, but the exact lineage pathway for differentiation of these cells from their progenitors is not fully understood. It is known from preliminary results that ceils resembling mesenchymal stem cells (MSCs) persist in human dermis throughout childhood and into the young adult, decreasing with age to undetectable levels after age 20. The dermal MSCs constitute populations of fibroblastic cells near the keratinocyte basement membrane at the dermaepidermal interface. close to vasculature in the reticular dermis, and adjacent to follicles in the papillary dermis.

Subcutaneous implants containing MSCs become highly vascularized within days, suggesting that the cells support vigorous angiogenesis. Implants with MSCs in bone and cartilage sites for tissue regeneration progress through the same stages of differentiation as those observed in the developing embryo using immunochemical markers, suggesting that the cells direct a true regenerative phenomenon in which the repair reiterates the ontogeny of the tissue.

The skin replacements of the invention use human MSC-derived dermal progenitors for the regeneration of dermis in conjunction with cultured human keratinocytes for the replacement of epidermis, forming a multi-layered, living skin equivalent. The use of MSC-based therapy is also a logical supplement to skin grafts, whether they are living skin equivalents, human cadaveric skin or autografts. MSC-based treatments add a regenerative element to the dermal layer underlying the epidermal keratinocytes, resulting in full-thickness dermal regeneration. This course of healing does not rely on passive infiltration of dermal progenitors into the wound site, but provides an active sources of dermal fibroblastic precursors. in addition, the MSCs signal a more rapid invasion of host vasculature. Both the active dermal regeneration and the increased angiogenesis ought to accelerate acceptance of the skin graft and integration with the surrounding host tissue. Therefore, the skin equivalent(s) of the invention offer a therapy that expedites healing with reduced scarring, and thereby reducing the period of hospital stay.

By combining the active dermal progenitor population with the demonstrated effectiveness of cultured human keratinocytes as an epidermal layer, the skin equivalent(s) of the invention create a more effective living skin equivalent than is currently available. Autograft skin will be unnecessary, since it is not necessary to sacrifice no healthy tissue from another site on the patient for either the autologous MSC preparation or the allogeneic keratinocytes. The ability to expand the MSCs in culture allows one to manufacture large amounts of skin equivalents from an initial marrow aspirate, so there is no prohibitory barrier to treating large wound or ulcer areas. By using MSCs as a source of dermal progenitor cells rather than differentiated cells. the potential risks associated with the de-differentiation of the implant are minimized. because it is possible to control the progenitor status of the MSCs. For example, ex vivo expansion of differentiated chondrocytes leads to the proliferation of de-differentiated fibroblastic cells that no longer make all of the specific chondrocytic markers, such as collagen It, and that fail in animal models of articular cartilage regeneration. However, culture-expanded MSCs that are implanted in osteochondral lesions of the removal condyle regenerate all the normal layers of subchondral bone, hypertrophic chondrocytes. and articular chondrocytes. In a similar manner, dermal regeneration is best accomplished by MSCs acting as progenitors of dermal fibroblasts, rather than by highly differentiated, committed cell populations.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed an a solvent or suspending medium.

The compositions of this invention can further include conventional excipients. i.e., pharmaceutically acceptable organic or inorganic carrier substances suitable for parenteral application which do not deleteriously react with the cells or active components. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can, if desired, be mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the cells or active components. For parenteral administration, particularly suitable vehicles consist of solutions, preferably oily or aqueous solutions, as well as suspensions, emulsions, or implants. Aqueous suspensions may contain substances which increase the viscosity of the suspension and include. for example, sodium carboxymethyl cellulose, sorbitol and/ or dextran. Optionally. the suspension may also contain stabilizers.

The following examples further illustrate but in no way limit the invention.

EXAMPLE 1

Mesenchymal Stem Cell Epitopes in Human Skin

The complex yet precise spatial arrangements in embryonic morphogenesis requires cells to express genes at specific temporal stages and at specific locales in order to acquire the structural and functional properties of the adult organism. Morphologic studies on the development of human skin reveal progressive increase in complexity and gene expression from undifferentiated embryonic precursors to end stage phenotypes seen in the adult. The continuum of events which characterize skin development have been aided by the use of markers which specify different stages or events in skin development (27). The use of cell surface markers and antigens have been especially valuable in evaluating the state of differentiation of the epidermis; since both structural proteins of the epidermis and cell surface markers of keratinocytes at various lineage stages are available (25, 27, 28). The use of these markers for epidermis have allowed a detailed spatial-temporal sequence of the structure and function of epidermal embryogenesis and development (24, 28).

Markers for the dermis, however, have been limited to extracellular matrix molecules associated with mesenchymal cells or more differentiated dermal fibroblasts. These include antibodies to specific collagens, elastin, proteoglycans, and other structural proteins of the dermis (27). Completely lacking however, are markers which can recognize dermal cells or stage specific subpopulations of dermal mesenchymal cells or fibroblasts. Markers for specific cells of the dermis which can be shown to be regulated in a spatial-temporal manner and at defined locales would provide valuable clues regarding dermal embryogenesis and the sequence of cutaneous development from the neonate to the adult.

The dermis develops embryonically from lateral plate mesoderm and the dominant cell type in embryonic dermis is the mesenchymal cell which later differentiates into the dermal fibroblast. (23, 42).There are some more differentiated fibroblasts among the mesenchymal cells which may be detected with their associated matrix components. However, other cells are multipotential and retain the ability to differentiate into smooth muscle cells which contribute to the vessel wall and the erector pilli muscle, adipocytes, and specific appendage related fibroblastic cells: some of them may even be recruited as endothelial cells.

Many investigators believe that mesenchymal cells persist into postnatal life as undifferentiated precursors of connective tissue cells (13). Mesenchymal stem cells in the adult organism are derived from embryonic mesoderm and are capable of giving rise to a variety of mesenchymal phenotypes including bone, cartilage,tendon ligament,marrow stroma, adipocytes, dermis, muscle and connective tissue (16). Support for this concept comes from studies which show that mesenchymal cells isolated from bone marrow or periosteum can form diverse phenotypes such as cartilage and bone when placed in the appropriate environment (For review see 40). Cell surface antigens on human marrow-derived mesenchymal stem cells have recently been detected by monoclonal antibodies (SH2, SH3, and SH4) specific to these multipotential progenitor cells. These antibodies also recognize rare cells in periosteum and dermis (21). Therefore, by using the SH2 marker for undifferentiated mesenchymal cells, the contribution of this cell to dermal development can be assayed.

In this study, we report the presence and distribution of a developmentally regulated antigen on the surface of a discrete population of undifferentiated mesenchymal cells in human dermis. The results indicate an important structural and functional role of mesenchymal stem cells in cutaneous development in specific locales as seen in epithelial-mesenchymal interactions in developing appendages, overlying epidermis, and vasculature.

Materials and Methods

Skin samples from autopsy specimens less than thirty six hours post mortem or from surgical procedures were obtained from the Human Cooperative Tissue Network at Case Western Reserve University. Sources of skin specimens included foreskin, abdominal, or breast skin. Age groups provided from this source ranged from day one to 84 years. These postnatal samples were plentiful such that many samples were tested (see results). Excess subcutaneous tissue and fat was carefully dissected from the specimens and unfixed tissues were embedded in OCT-Tissue Tek Freezing Medium, frozen in liquid nitrogen, and stored at −20° C. Frozen sections 6 μm thick were placed on gelatin coated slides and air dried.

Embryonic sources of human skin cryosections were generously provided by Dr. Karen Holbrook from the departments of Biological Structure and Medicine, University of Washington: Seattle, Wash. At least three different specimens from each described cohort (see results) was examined for these samples. Age groups tested ranged from 58 day estimated gestational age (EGA) of human fetuses through 140 day EGA.

Generation of antibody markers to human mesenchymal stem cells has been previously described by Haynesworth and will not be described here. The SH2 antibody was generously provided by Dr. Haynesworth for use in these studies (21). Tissue sections were incubated with primary antibody for 1 hour at room temperature in a high humidity chamber. Culture supernatant was used undiluted. Following the incubation, slides were rinsed three times with 0.1% BSA-PBS, and then incubated for one hour with 75–100 μm of fluorescein isothiocyanate (FITC)-conjugated goat-antimouse IgG (Organon Teknika), which had been diluted 1:2000 in 0.1% BSA-PBS. The slides were rinsed three times with 0.1% BSA-PBS and cover-slipped with a drop of PPD immunofluorescence mounting medium (Eastman Kodak, Rochester. N.Y.), and observed on an Olympus BH-2 epi-fluorescence microscope. Negative control slides consisted of identical analysis of sections with culture medium that did not contain antibody or the SB1 chick antibody (55) which does not cross-react with human tissue but is of the same isotype as SH2 antibody. Other antibodies utilized in this study include the nerve specific antibody HNK-1 which recognizes an acidic glycoprotein on human peripheral nerves, central and peripheral nervous tissue, myelin sheaths, oligodendrocytes, schwann cells, neurons, and some astrocytes (12, 17, 29). Monoclonal mouse anti-human Factor VIII-related antigen (DAKO) was also utilized to recognize endothelial cells and vascular tissue. Positive controls consisted of analysis of sections with the antibody 6E2 which was generated by Haynesworth and is a human specific monoclonal antibody which reacts with a large variety of human tissues.

Results

This immunohistological study examined the spatiotemporal distribution of epitopes in developing and postnatal human skin using a monoclonal antibody which recognizes human mesenchymal stem cells. Immunostaining was performed on skin specimens from day 78 EGA through the age of 84 years. Specimens from third trimester (greater than 180 day EGA) were not available. Immunoreactivity involving several layers or structures in skin from most superficial to deeper levels was examined including the epidermis, developing hair germs or hair follicles. the dermal/epidermal junction, the upper half of the dermis, vasculature plexus in the deep dermis, and the lower half of the dermis including the portion adjacent to the hypodermis. Positive immunoreactivity in all specimens was scored when a selective, bright green fluorescent staining pattern could be visualized which reflects the presence of reactive epitopes. Autofluorescence of the stratum corneum or dermal and subcutaneous fibers was occasionally seen as a yellowish color which could be easily distinguished from the bright green fluorescence seen with FITC excitation.

For simplicity, skin embryogenesis and maturation has been regimented into specific periods of development based upon significant dermal or epidermal temporal landmarks related to morphogenesis. A brief review of these developmental periods is provided with our results.

Cellular Dermis. This stage is comprised by a predominantly cellular dermis with a relatively smaller associated matrix compared to later periods of cutaneous development. By 8–9 weeks, there is a transition between embryonic and fetal stages of skin development (36). The undifferentiated mesenchymal cell is the predominant cell of the dermis and it is enmeshed by a loosely organized the extracellular matrix of fine fibrillar components and a gelatinous mixture of glycosaminoglycans and collagens. The dermis is delineated from the subcutaneous region (hypodermis) by a vascular plane (36). The overlying epidermis is marked by stratification into a simple epithelium of periderm and basal cells associated with a basement membrane (23). Epidermal appendages have not yet formed. Positive immunostaining by the SH2 antibody is observed as discrete cell surface staining to cells in close approximation to the lumen of vasculature in the deep portions of the dermis. These mesenchymal cells or perivascular cells tend to be oriented parallel to the surface epidermis. There is also immunostaining to discrete cells in the vascular plane at regularly spaced intervals. There is absence of immunostaining in the layers above the vascular plane of the dermis including the epidermis.

Cellular to fibrous transition. This stage, which occurs near the end of the first trimester, is characterized by transition of the dermis from a cellular to a more fibrous tissue. The initiation of follicle morphogenesis commences during this period at approximately 11 weeks. (28).The hair germ (the earliest recognizable follicle precursor) is seen as foci of basal epidermal cells which bud into the dermis and are surrounded by collections of aggregated mesenchymal cells. The dermis has begun to accumulate a fibrous matrix via enlargement of collagen fiber bundles (36). Immunostaining with the SH2 antibody reveals reactivity to cells lining the vasculature in the deep dermis in and scattered reactivity to other mesenchymal cells in the deep dermis. Reactivity is also seen to rare scattered cells in the upper half of the dermis again at fairly regularly spaced intervals. There is no positive immunostaining to cells below the basement membrane of the epidermis or to mesenchymal cells associated with emerging hair germs.

Fibrous dermis. The dermis in this period is distinctly a fibrous connective tissue, with developing epidermal appendages extending deeply within the dermis. Vessels and nerves with connective tissue sheaths course throughout the dermis (44). There is a subpapillary vascular plexus which branches into the papillary dermis. The deep dermis boundary with the hypodermis is defined adipose and subcutaneous connective tissue (44). The distinction between the papillary and reticular dermis becomes more apparent mostly due to differences in size between collagen bundles in the two layers. Immunostaining with the SH2 antibody showed collections of cellular reactivity identified in precise locations including: subepidermal mesenchymal cells near the basement membrane below the epidermis, unique cells at the base of developing hair germs and follicles, cellular reactivity in perivascular regions of the deep dermis and subepidermal microvascular plexus, and scattered reactivity to single cells or groups of cells in the deep dermis.

Neonatal Dermis. Postnatal dermis within the first two years of birth has all of the morphological landmarks associated with adult skin including well established papillary and reticular layers as well as fully formed epithelial appendages. It differs from embryonic skin due to the latter's decreased dermal thickness, fibril diameter, ratio of type I to III collagen, and higher water concentration (26). Immunofluorescence with the SH2 antibody reveals reactivity to discrete cells in close proximity to the dermal/epidermal junction below the basement membrane of the epidermis. Reactivity is noted only in the papillary dermis with epidermis and reticular dermis lacking reactive cells. There is a decreased number of immunoreactive cells in these specimens compared to embryonic skin.

Adult Dermis. Beyond age 30, there is a complete absence of immunostaining with the SH2 antibody. A total of 69 postnatal specimens were immunostained. There were 30 male and 39 female samples stained with no significant differences among age groups greater than age 5. Eleven of a possible eleven foreskin samples all less than age 5 exhibited reactivity. Only one of four abdominal samples from groups less than age 5 exhibited immunoreactivity. The immunoreactivity seen in the 21–30 age group represented a sample of female breast skin.

Lack of immunoreactivity to the SH2 antibody in these older age groups probably cannot be explained on the basis of epitope masking since experiments were performed using several extracellular matrix digestive enzymes including hyaluronidase, trypsin, chondroitinase, and collagenase. Digestion of the extracellular matrix did not unmask epitopes which immunostained with the SH2 antibody (data not shown).

Nerve and vascular markers. To confirm that the SH2 antibody staining was indeed to cellular components of vasculature organelles, an antibody to Factor VIII related-antigen was utilized. Anti-Factor VIII-related antigen antibody immunostaining revealed reactivity to vascular organelles in the deep dermis corresponding to the deep vascular plexus in developing skin. It was difficult to discern if some of the reactivity to lining cells of the vasculature (endothelial cells) were the same cells which reacted with the SH2 antibody. Clearly the SH2 antibody reacts to some perivascular cells. However, it is possible that the SH2 antibody reacts with some of the outer connective tissue sheath components of the vasculature and or some endothelial cells. The nerve specific HNK-1 antibody was utilized to determine if SH2 positive cells in developing skin were reactive with cells of the nervous system. Subepidermal immunoreactive cells stained with the HNK-1 antibody. The morphology of the HNK-1 antibody revealed long slender, almost linear, cellular reactivity. The most proximal portion of developing hair follicles also reacted with this antibody. Both of these patterns were clearly distinguished from the pattern noted with SH2 immunoreactivity.

Discussion

The results demonstrate that there are epitopes to marrow-derived mesenchymal stem cells present in human skin and that the spatiotemporal distribution of these cells changes with development and age. Specifically, the number of immunopositive cells and the foci where these cells reside declined with age. Our interpretations of the spatiotemporal patterns of the Mesenchymal Stem Cell epitope is summarized in Table 2. Precise locations including subepidermal mesenchymal cells near the basement membrane, unique cells at the base of developing hair germs and follicles. scattered reactivity in deeper layers of the dermis, and groups of cells in close association with developing vasculature were identified in embryonic samples through the second trimester. In postnatal skin, mesenchymal stem cell reactivity was noted in rare cells in the papillary dermis near the dermal-epidermal junction in close proximity to the basement membrane. These epitopes were recognized in approximately 80% of young-aged specimens age 0–20. Samples greater than age 20 rarely showed any positive immunostaining pattern. Importantly however, reactivity to cells in the deeper regions of the dermis was not visualized. in marked contrast to embryonic skin samples. There was no regional or anatomic variability in terms of immunostaining pattern in positive samples though areas taken from foreskin of postnatal samples most consistently exhibited reactivity.

Observations using human fetal tissue revealed positive immunostaining to cells of the subepidermal mesenchyme. There was quantitatively more cells in this region which were immunopositive in comparison to postpartum samples as well as a greater distribution along the length of the subbasement membrane region. Again, immunopositive cells were noted in deeper areas of dermis in fetal skin when compared to postpartum skin. Particularly, there was immunostaining to discrete cells at the base of developing hair follicles or hair germs and reactivity to groups of cells in the deep layers of dermis in close proximity to lining cells of the vasculature. The cells in which SH2 identified did not co-localize with dendritic cells of the nervous system based upon experiments with the HNK-1 antibody which recognizes nervous tissue. It is therefore doubtful that the cells which SH2 recognizes in the upper dermis are of the nervous system family. Immunostaining with the factor VIII-related antigen antibody shows that the SH2 antibody likely reveals cells related to developing vasculature as the SH2 antibody and the factor VIII-related antigen antibody recognize structures interpreted to be vasculature. However, factor VIII-related antigen is a marker that becomes more prominent with the degree of maturation of the microvasculature in developing skin and has been hypothesized as a marker for endothelial cell differentiation (49). Therefore, it may not recognize all undifferentiated precursor vascular cells especially at early developmental periods.

It is clear from the data that there are epitopes to human mesenchymal stem cells in human skin and that there is a specific developmental distribution of the identified cells. Differences in immunoreactivity patterns of epitopes to human marrow-derived mesenchymal stem cells at varying developmental stages support the hypothesis of a dermal repository for mesenchymal stem cells which. based upon their locale, likely play critical functional roles in the dermal-epidermal interaction of developing hair follicles, overlying epidermis, and vasculature. These roles likely include secretion of various autocrine and paracrine cell-signalling molecules and maintenance and elaboration of the extracellular matrix important for the physical properties of the dermis.

We have focused on the morphogenesis of developing skin in temporal sequence, such that precise alterations in groups of cells can be appreciated. The emergence and abatement of the SH2 epitope with development and aging of skin tissues, and the observation that a distinct subpopulation of dermal fibroblasts and; mesenchymal cells are immunopositive, suggest evidence of a phenotype specific marker of dermal development. The existence of an epitope which recognizes mesenchymal stem cells in skin may have its origins from dermal embryogenesis since components of dermis originate from cells of superficial dermatome segments of somite mesoderm and from mesenchymal areas of the body subjacent to the skin. (23). This sub population of dermal fibroblasts, expressing stage specific phenotypically distinct molecules on their surface, likely represents a progenitor or early stage in the continuum of developmental and stage specific variants. This developmental progression, called a lineage, frequently exhibits specific cell surface epitopes which are immunologically detectable (16). We suggest that the cellular antibody staining represents precursor cells of the dermal fibroblastic lineage, specifically to mesenchymal stem cells. The epitope which the SH2 antibody recognizes, is a sub-population of mesenchymal cells which have been shown to form diverse phenotypes such as bone and cartilage when placed in the appropriate environment (21, 22).

Furthermore, the results suggest that dermal development may proceed from the most distal locations to the more surface or proximal locales similar to the differentiation of stem cells that occurs in the epidermis (20). This is suggested by data which indicate an abundance of immunopositive mesenchymal stem cells in the deepest portions of dermis and at the vascular boundaries which separate dermis from hypodermis in the first trimester; and apparent migration of these cells more proximally to the epidermis during embryonic development and at early postnatal ages.

Also, the significance of the locales where mesenchymal stem cells reside in skin must be considered. The development of the hair follicle represents a complex mesenchymal-epithelial interaction. Hair germs, the earliest recognizable precursors of follicles, represent a foci of basal epidermal cells which bud into the dermis near collections of particular mesenchymal cells spaced regularly beneath the dermal-epidermal junction (28). It is known that some of these cells express different markers when compared with cells of the dermal mesenchyme (51). Hair germs later develop into Hair peg by the second trimester with the terminus forming into a bulblike structure. The epithelial cells of this structure later give rise to the inner root sheet and fiber and the surrounding mesenchymal cells later organize into the dermal papilla (28). Interestingly, these dermal papilla cells which are of mesenchymal origin have been clearly shown to induce follicle formation and to determine hair growth and hair quality (52, 53).

Mesenchymal stem cell antibody reactivity was noted to be in close approximation to microvasculature of the dermis. The undifferentiated mesenchymal cell seen in embryonic dermis likely gives rise to the vascular endothelial cell and probably the pericyte (13). The precursors of endothelial cells, smooth muscle cells,and other specialized cells of vasculature are presumed to be perivascular mesenchymal cells (37, 39). One would expect these precursors to be in close proximity to their differentiated progeny; the microvasculature and vasculature itself (41). It is also known that perivascular mesenchymal cells are implicated in angiogenesis and the initial phases of capillary sprouting (54). It seems likely, based upon their anatomic location, that the mesenchymal cells located in close proximity to vasculature are undifferentiated precursors that participate in angiogenesis. Indeed, it is known that the pericyte ,derived from the mesenchyme, can exhibit pluripotentiality and may be precursors to cellular phenotypes such as osteoblasts and smooth muscle cells, (15, 39)

The data also suggest an age related change in reactivity to epitopes of human marrow derived mesenchymal stem cells. Results reveal a decreased number of mesenchymal stem cells with age. This is entirely reasonable due to the tremendous morphologic and growth requirements of embryonic and neonatal cutaneous development. A decline in the number of mesenchymal stem cells with age has been seen in other tissues such as bone marrow and the diminution of these cells may partially explain the decreased capacity for and amount of osteogenic tissue in this organ with age. One can postulate that this decreased number of mesenchymal stem cells would have metabolic consequences on the skin since cells which reside in dermis have many regulatory functions on epidermal proliferation and maintenance. Cutaneous changes in skin which are known to be associated with aging include flattening of the dermal-epidermal junction. decreased epidermal turnover, increased disorder and heterogeneity of epidermal keratinocytes. and changes in extracellular matrix components such as collagen and elastin (19 32 34, 48).

One assumption of this study is that epitope which recognizes human marrow derived mesenchymal stem cells also recognizes the same cell type in human skin. We believe that the specific locales of epitope reactivity to regions where pluripotential cells and complex mesenchymal-epithelial interactions occur is not a coincidence. The locales of epitope reactivity clearly make anatomic and functional sense for an undifferentiated cell of mesenchymal origin. Although this study depends on precise immunohistochemical and histological observations,future studies need to be performed in which these cells are isolated and proven to exhibit phenotypic characteristics of the mesenchymal stem cell derived from bone marrow. These tests may include the presence or absence of other immunological markers and/or the ability to form multiple phenotypes when placed in the appropriate environment.

EXAMPLE 2

Establishment of in Vitro Systems for Differentiating MSCs into Dermal Fibroblasts This series of studies is directed to development of reagents that distinguish human dermnal fibroblasts from MSC. These reagents (antibodies, oligonucleotide probes, responses to growth factors) are screened against developing skin (e.g. embryonic skin spheroids, frozen sections of fetal tissues) to determine if these markers of MSC differentiation correlate with nominal development. Once markers are selected, MSCs are treated in vitro in cell culture under conditions that promote their differentiation in a dermal lineage (e.g. by varying media, matrix molecules, soluble growth factors, co-cultured cells). Components required for dermal differentiation to produce a routine, defined media in which quantitative assays of dermagenesis can be performed are identified. Ultimately, markers of dermal differentiation for the MSCs are then compared to human cell lines of papillary and reticular dermal origin to distinguish these two subtypes among the MSC progeny.

The production of reagents that distinguish markers of dermal differentiation involves monoclonal antibody isolation and molecular cloning strategies. Antibody methodologies capitalize on those that have been successful in other mesenchymal lineages. most notably that for osteogenic differentiation. Cell surface antigens targeted initially by immunizing mice with whole cell preparations or plasma membrane fractions of human dermal fibroblasts. These cells can either be derived from primary tissue explants or from human cell lines that are available as described infra. Screening of the immune sera and, subsequently, hybridoma supernatants is performed on primary cultures of undifferentiated MSCs versus dermal fibroblast lines. Antibodies specific to dermal cells over MSCs are carried further to secondary screens using human fetal neonatal immature and adult skin biopsies in frozen sections by immunofluorescence. While screening microscopically on tissues is tedious, it permits the selection of those antibodies that most closely reflect the normal differentiation of dermis in vivo.

Selected antibodies are used to purify their corresponding antigen from dermis and dermal cell lines by immuno methods. Partial sequence analysis of the antigen will be adequate to identify the protein, if known, from existing sequence databases. Otherwise, the cDNA will be identified by standard molecular cloning procedures from dermal fibroblast cDNA libraries. In cases where the antigen is not a protein (e.g. carbohydrate), standard analytical chemistry techniques are utilized for chemical composition and mass spectrometric determinations.

Molecular approaches to identifying novel cDNAs are performed, in parallel to the antibody development. These experiments include: 1) screening MSCs and dermal fibroblast cell lines for known families of molecules by RT-PCR and direct oligonucleotide probes of Poly A$^+$-RNA using degenerate probes. This is done to determine novel molecules that are members of known groups, such as the TGF-β receptor superfamily, integrin family, immunoglobulin/cell adhesion molecule superfamily, etc. As these screens continue, differential display techniques identify cDNAs found in dermal cells but not in MSCs. Partial DNA sequence will be sufficient to identify novel molecules from those already known, although novel isoforms of or splice variants of known require more extensive analysis. For the novel molecules identified, polyclonal antibodies are prepared in rabbits either to bacterial expressed recombinant fusion proteins or to synthetic peptide antigens. These antibodies are useful used to confirm the presence of the protein product in dermis.

Primary cultures of human MSCs are exploited to set up dermal differentiation assays in vitro. Briefly, iliac crest marrow aspirates (20 ml) are obtained from volunteer donors, and filtered to remove bone chips. The cell suspension is layered on a Percoll step gradient of 1.073 g/ml density, and the interface fraction is collected. The cells are plated in plastic tissue culture flasks for MSC selection and expansion. When the cells become 80–90% confluent, they are trypsinized, washed. and replated at a density of 1:3.

Preliminary studies have established that inhibitors of the cell division cycle, known as cyclin-dependent kinase inhibitors (cdki) are expressed very early upon commitment of the MSCs to differentiation. Luciferase reporter gene constructs have been prepared under control of the promoter of one of these cdki genes,. the p21 (cip 1, wafl). These constructs are transfected into the MSCs by electroporation, and molecules forcing a commitment in the MSCs are screened rapidly for their ability to express luciferase. Subsequently, established cell surface and matrix markers of dermal cells are used as a secondary confirmation of differentiation.

Critical to identifying differentiation factors in this system is the development of culture media and additives that promote long-term survival of the differentiated cells. The list of additive candidates includes polypeptide growth factors that are known to act on MSCs in other culture systems, such as PDGF and members of the TGF-β superfamily. Matrix proteins that may promote MSC differentiation include fibronectin, which is known to be highly regulated during skin development. For example, the expression fibronectin produced by the MSCs by Northern analysis is quantified, and the dose-dependence of fibronectin as an additive to the media or directly to the collagen gel studied. In concert with these studies, the integrin profiles of the cells are monitored to determine the profile of potential fibronectin and collagen receptors. Primary MSC preparations are known to be negative for α4 and for β2 integrins, for example, but dynamic changes can occur for these and other surface markers. The secreted proteoglycan profile is analyzed using existing monoclonal antibodies.

An alternative approach is co-culture of MSCs with human keratinocytes. Preliminary data indicates that MSCs can support keratinocyte growth, suggesting that the keratinocytes produce factors that cause the MSCs to differentiate into a dermal fibroblast or dermal precursor cell. Direct co-cultures are performed, and, in parallel experiments are conducted with keratinocyte conditioned media. irradiated keratinocyte cultures, and plates conditioned with matrix laid down by keratinocyte cultures. Molecules from the keratinocyte cell surface or conditioned media or conditioned matrix are isolated in bulk from large scale cultures. and characterization of the protein components are carried out.

EXAMPLE 3

MSCs Support Keratinocgte Growth in Vitro to Produce a Living Skin Equivalent These studies address the development of an in vitro dermal differentiation model to the point where the progeny of MSCs can be demonstrated to support human keratinocytes in a multilayered system. The strategy for experimentation is as follows: first, functional assays of the MSCs to confirm their ability to act as a feeder layer for keratinocytes, second, gel contraction assays to confirm the ability of MSCs to contract collagen gels as do papillary dermal fibroblasts; and third, growth of MSC-derived dermal cells in submerged collagen gels with and without the addition of a keratinocyte ,layer.

Functional Assays

The initial assay for the MSCs is a modification of the Rheinwald-Green system [9] where irradiated stromal cells act as a feeder layer for keratinocytes. Dermal cell lines from the papillary or dermal layers of skin from 22-month and 51-year old patients were obtained. The dermal cells or MSCs. seeded at approximately $10^5$ per 100-mm dish received 5100 rads from a Cobalt source. The cells cease proliferating but remain alive. Foreskin keratinocytes were seeded on the dishes at low density (2000 cells per dish) and cultured in media [9] for 9 days. Keratinocyte colony counts were performed after crystal violet staining. Preliminary studies indicate that papillary dermal cells and MSCs support similar numbers of keratinocytes, and these are significantly higher than the numbers of colonies supported by reticular dermis cells.

The collagen gel contraction assay is used to monitor the rate at which the MSC-derived dermal cells contract floating type I collagen gels. During the first 48 hours of plating in collagen gels, reticular dermal cells show significantly higher rates of gel contraction, compared to papillary dermal cells. Therefore, as a criterion of differentiation, the MSCs and their progeny are tested to see if their rate of gel contraction more closely resembles the papillary or the reticular rate. Presumably, similarity to the papillary dermal cells will correlate with effective support of keratinocyte cultures.

Optimization of Cell Co-Culture

Conditions from the in vitro systems for MSC differentiation was optimized to promote keratinocyte growth in co-culture. This involves the dose and time dependence of all soluble polypeptide factors, as well as the basal media components. Examples of the details of these studies include individual media formulations varying amino acids, vitamins, ions, steroids, and lipids. The goal is to optimize conditions for an unirradiated culture of MSC-derived dermal cells to support foreskin keratinocyte growth. Ultimately, the multi-layer co-culture was raised to the air-water interface to initiate cornification of the epidermal surface.

EXAMPLE 4

Construction of a Bi-Layered Dermal Eguivalent Containing Human Papillary and Reticular Dermal Fibroblasts Dermal equivalents containing fibroblasts from humans, or other species, are known (56–61). While these dermal equivalents support keratinocyte proliferation and differentiation, their designs are improved by mimicking the natural bilayered configuration of the dermis which consists of two morphologically and functionally distinct layers, the papillary dermis and reticular dermis. (62) The relatively thin and highly cellular papillary layer is situated immediately subadjacent to the basal lamina and epidermis while the deeper and densely collagenous reticular layer comprises the bulk of the dermis. Each of these two dermal layers contains intrinsically different populations of cells. (63–66). Very little is known about how these cells, independently or in various combinations, support keratinocyte proliferation and differentiation. This example shows the construction of a bilayered dermal equivalent that contains papillary and reticular dermal cells, each in defined layers. These cells maintain their positions within their respective layers.

The studies undertaken here demonstrate the feasibility of constructing a layered dermal equivalent. Matched human papillary and reticular dermal cell lines (i.e., from the same individuals) were used to construct dermal equivalents by seeding these cells into type I collagen gels. as random mixtures. or as defined layers. In order to trace the movements of these different populations of dermal cells, it was necessary to develop a technique to differentiate these cells once they had been seeded into the gel. Therefore, we explored the use of fluorescent vital dyes 1,1'-dioctadecyl-3,3,3',3'-tetramethylindocarbocyanine perchlorate; $DiIC_{18}$(3) (DiI) and 3,3'-dioctadecyloxacarbocyanineperchlorate; $DiOC_{18}(3)$ (DiO) to provide the means of specifically and separately labelling papillary and reticular dermal cells and monitoring their movements within collagen gels.

These labelling procedures meet two fundamental criteria. First, cells retain the label for the duration of the study. Second, the physiology of labelled cells is not compromised. There was no sorting of papillary and reticular cells in gels containing mixed populations of cells, and papillary and reticular cells, when seeded into layers, remained in their respective layers. Therefore, it is possible to re-create the natural configuration of the dermis in dermal equivalents.
Materials and Methods
Papillary and Reticular Dermal Fibroblast Cell Lines Two different papillary and reticular dermal cell lines (provided by Dr. I. A. Schafer, MetroHealth Medical Center, Cleveland, Ohio) were used for these studies. One matched set of cell lines was established from a 51-year individual (lines 4 Papillary and 4 Reticular) and a second matched set was established from a 22-month individual (lines 6 Papillary and 6 Reticular). Details for the isolation and culture of matched papillary and reticular cell lines have been published. (6) Briefly, a dermatome is used to obtain the upper layer of skin from the upper inner aspect of the arm at a depth of 0.38 mm and fibroblasts grown from this upper layer constitute the papillary population of cells. The remaining dermis is dissected to the hypodermis and fibroblasts grown from this layer constitute the reticular population of cells. Papillary and reticular dermal cells have been characterized according to their morphology in monolayer culture, growth kinetics, packing density at confluence and relative abilities to contract type I collagen gels. (66)

Assays for both matched sets of dermal cell lines were performed concurrently. As might be expected for the divergent ages of the donors (66) the growth kinetics and gel contraction kinetics for the two sets of cell lines differed from each other. However, the presence of the vital dyes did not significantly alter the growth characteristics or the gel contraction characteristics of either matched sets of cells. For the sake of simplicity, only one set of data is presented, that from the 51-year individual.

Carbocyanine dyes DiI and DiO were purchased from Molecular Probes, Eugene, OR. A 2 mg/ml stock solution of DiI in absolute ethanol was prepared in advance and was stored at 20° C. Immediately prior to use, the stock was diluted 1:250 in Dulbecco's modified Eagle's medium supplemented with 10% fetal bovine serum (complete DMEM). Medium withdrawn from monolayer cultures of dermal cells was replaced with complete DMEM containing the dye, and the cultures were incubated for various time periods; an overnight incubation at 37° C. in a humidified atmosphere containing 5% $CO_2$ and 95% air was found to be optimal. The medium containing the dye was removed and any excess dye was removed by two rinses with sterile Tyrodes's solution. Labelled cells were maintained on the culture dishes until required for studies; normally, these cells were used immediately after labelling. At this point, they were detached from the dishes with 0.25% trypsin-1 mm EDTA, Life Technologies, Grand Island, N.Y. The cell pellet was washed twice with complete DMEM before replating; however, those cells that were to be incorporated into type I collagen gels were washed and resuspended in serum-free DMEM.

A saturated solution of DiO was prepared by adding 1–2 mg of dye to 1 ml of absolute ethanol and the stock solution was stored at 4° C. Immediately prior to use, the stock solution was centrifuged and an aliquot of the supernatant was diluted 1:20 in serum-free DMEM. Cells released from culture plates with 0.25% trypsin–1% EDTA were washed twice with serum-free DMEM, and the pelleted cells were resuspended in the diluted DiO and incubated for various time periods; an incubation of 10 minutes at room temperature was found to be optimal. The stained cells were washed twice with complete DMEM prior to plating or with serum-free DMEM if the cells were to be incorporated into a collagen gel.
Determination of Cell Number Unstained papillary and reticular dermal fibroblasts were seeded, in duplicate, onto 35 mm culture dishes at densities of 50, 100, 150, 200 and $250 \times 10^3$ cells per plate. Cell numbers were determined from hemocytometer counts. The initial plating efficiencies varied for papillary and reticular cells: however, by two days, the numbers of cells per plate was equal to that for the initial inoculum. Therefore, day two was used for the generation of standard curves.

Cell numbers were determined by the crystal violet assay. Monolayer cultures were fixed on the plate for 15 minutes with 1% glutaraldehyde in Tyrode's balanced salt solution, washed with water, and air dried. The cells were stained with 0.1% crystal violet for 30 minutes and were washed three times-with water to remove the excess dye. After air drying, the dye was extracted with 1% Triton X-100 in water. The absorbance of the crystal violet dye extract was read on a spectrophotometer at 600 nm. Neither DiI nor DiO absorb light at 600 nm: therefore, their presence does not affect the crystal violet assay. Standard curves for each cell line were prepared from the averages of these readings. As extrapolated from these standard curves, the absorbance value for 250,000 papillary cells was 0.942, while that for reticular cells was 1.166.

Collagen Gels

Type I collagen, acid extracted from bovine skin, was purchased from Gattefosse (Saint-Priest, France). This product contains 3 mg/ml collagen, of which 95–97% is type I. Prior to use, the collagen was dialyzed at 4° C. against water adjusted to pH 3.0 with HCl and was sterilized under UV light for 2–3 hours while maintaining the temperature at 4° C. Papillary and reticular fibroblasts, either unlabelled or labelled with DiI or DiO, were suspended at room temperature in serum-free DMEM. A 1.5-ml aliquot of cell suspension was mixed with a 1.5 ml aliquot of cold collagen. This mixture was quickly poured into wells of 6-well (35-mm wells) culture dishes, Costar, Cambridge, Mass. The plates were incubated at 37° C. for 15 minutes to allow the collagen to gel. Just enough DMEM+10% FBS was added to wells to cover the gels (about 1 ml). Bilayered gels were prepared in the same manner as described above, except 0.75 ml each of cell suspension and collagen were used for each layer. The first layer was allowed to gel for about 15 minutes, and the second layer was poured over the first layer. The gels were detached from the plastic using a sterile, flat weighing spatula, then an additional 1 ml of medium was added to each well. Plates containing floating gels were incubated at 37° C. in a humidified atmosphere containing 5% $CO_2$ and 95% air with medium changes every 4 to 5 days. The extent of gel contraction was determined by measuring the diameter of the gels; three replicate gels were measured for each experimental set. At the termination of the gel contraction study, one gel from each set was processed for histological examination. Half of each gel was fixed for 4 hours at 4° C. in 10% formalin in 0.1 M phosphate buffer at pH 7.4. (71) Fixed and unfixed gels were frozen in Tissue-Tek O.C.T. embedding medium (Miles Scientific, Elkart, Ind.) and 8-$\mu$m cryosections were cut and stored frozen until immediately before the slides were viewed. Coverglasses were mounted with a glycerin-based mounting medium containing phenylenediamine. (72)

Other collagen gels taken at weekly intervals, up to five weeks, were cut in half. Half of the gel was immediately embedded in O.C.T. embedding medium, and half of the gel was fixed overnight in buffered 10% formalin before being embedded in O.C.T. medium. Without prior fixation, the dyes diffused rapidly out of the sectioned cells when a coverglass was mounted. Although labelled cells could be identified, better result were obtained from samples that had been fixed in formalin for a minimum of 30 minutes.

All photographs were taken on an Olympus BH2 photomicroscope with fluorescein or rhodamine filter sets and Kodak Tmax ASA 400 film.

Results

Labelling Dermal Cells with DiI and DiO Dye Longevity Studies

Human cell lines, established separately from the papillary dermis and reticular dermis, were incubated in the presence of DiI and DiO vital dyes, which resulted in all cells being labelled. Cells labelled with DiI appeared bright red when viewed with a rhodamine filter, although most of these cells could also be seen with the fluorescein filter in place, but with greatly attenuated intensity. With some fluorescein filters, DiI-labelled cells appeared yellow which allowed them to be discriminated from the green DiO-labelled cells and from cells immunolabelled with fluorescein isothiocyanate-conjugated antibody. With other fluorescein filters, DiI-labelled cells appeared green. but could still be identified by virtue of their visibility when viewed with both rhodamine and fluorescein filters. Four cells are present in the microscopic field in FIG. 1. In panel A, the photograph was taken with the fluorescein filter in place and all four cells are visible. However, the DiO-labelled cell indicated by the arrow in panel A is no longer visible (see panel B) when the rhodamine filter is in place. The intensity of the DiI label is an important factor in its visualization with the fluorescein filter in place. Intact cells. as shown in FIG. 1, emit a stronger signal for DiI than do sectioned cells where it is often possible to clearly discriminate between DiI- and DiO-labelled cells by switching filters.

The longevity of the dyes was studied under two situations: in cells grown as monolayers and in cells incorporated into type I collagen gels. When dermal fibroblasts are seeded onto plastic culture dishes, they attach and divide until they attain confluence. As these dyes are diluted upon cell division, it is important to determine whether sufficient amounts of dye are retained at confluence. In contrast, when adult dermal cells are seeded into type I collagen gels, cellular proliferation is substantially suppressed. (73–75) In this situation, any dye loss that might occur would be due to metabolic factors, such as membrane or organelle turnover.

When seeded at low density, dermal fibroblasts continue to divide for periods up to 12 days, by which time the cultures have become confluent. Under the conditions employed in this study, papillary dermal cells typically undergo 6 to 7 cell divisions. Following such divisions, the percentages of intensely stained, moderately stained, and unstained cells were determined by trypsinizing cells from culture plates and replating them onto microscope slides at a lower cell density suitable for counting (Table 1).

TABLE 1

DiI- and DiO-labelling in Actively Dividing Dermal Fibroblasts

|  | DiI-labelled | | DiO-labelled | |
| --- | --- | --- | --- | --- |
| Papillary Cells | | | | |
| Intensely Labelled | 143[a] | 46[b] | 42 | 14 |
| Weakly Labelled | 171 | 54 | 104 | 65 |
| Unlabelled | 0 | 0 | 63 | 21 |
| Reticular Cells | | | | |
| Intensely Labelled | 77 | 51 | 13 | 7 |
| Weakly Labelled | 74 | 49 | 130 | 69 |
| Unlabelled | 0 | 0 | 45 | 24 |

[a]Number of cells counted.
[b]Percentage of total cells counted. Initially, all cells were labelled. The percentage of labelled cells shown here was determined on day 14 after labelling.

For papillary dermal cells, which grow at a faster rate than do reticular dermal cells, all cells continued to be labelled with DiI after 6 to 7 cell divisions. However, the DiO-labelled cells have diminished intensity with only about 60–70% of the cells stained with DiO scored as labelled. Both dyes appeared to be diluted by cell division, but these observations indicate that cells can undergo several divisions without significant loss of dye. The longevity of DiI appears to be superior to DiO, possibly because of its higher excitation intensity and/or perhaps because higher amounts are taken up by cells. There was no detectable change in cell morphology consequent to staining with either dye.

Labelled cells incorporated into type I collagen gels were cultured for periods up to 5 weeks. Microscopic examination of frozen sections of fixed gels revealed that all of the labelled dermal cells continued to be stained. This indicates that there is minimal loss of dye due to metabolic turnover of cell membranes and cytoplasmic organelles that retain these dyes under the conditions reported here.

Growth Kinetics of Labelled and Unlabelled Papillary and Reticular Dermal Cells

Figure 2B:
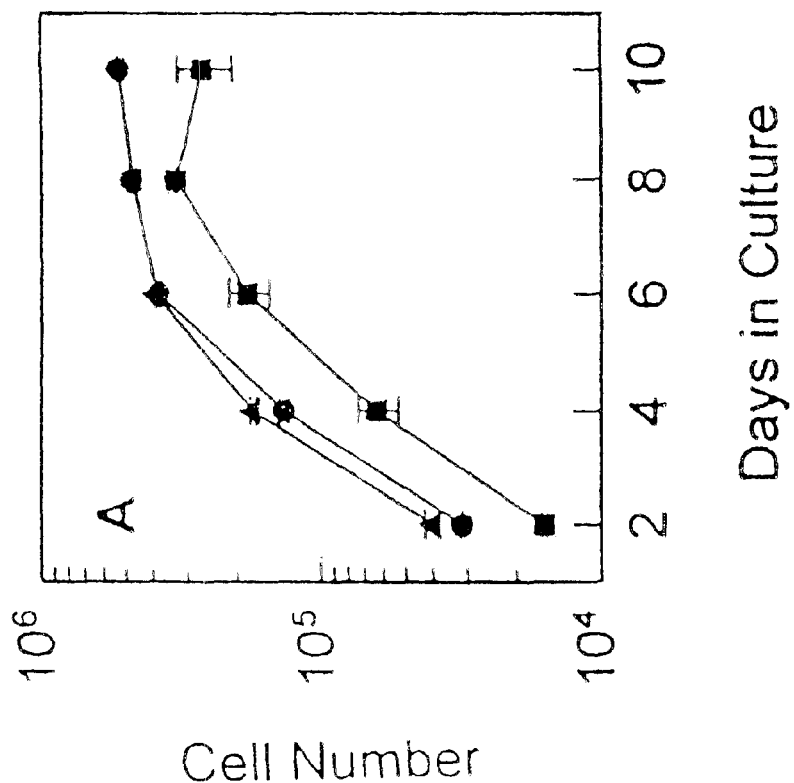

Growth curves were determined by plating 30,000 cells in triplicate onto 35-mm culture dishes and, on days 2 through 10, using the crystal violet assay to measure cell numbers. (69, 70). The data used to generate the growth curves shown in FIG. 2 were statistically analyzed using the paired t-test and the values for the DiI- and DiO-labelled cells were found not to be different at the 95% confidence level. Thus, cells labelled with these vital dyes grew at the same rates as did their unlabelled counterparts. There was an apparent decrease in the number of DiO-labelled papillary dermal cells on day 8. Although this decrease was not statistically significant at this time point. it appears to indicate the start of a process whereby DiO-labelled dermal cells begin to detach from the plate. This process intensifies when cells are cultured for longer periods of time.

Construction of Dermal Equivalents Using DiI- and DiO-Labelled Dermal Cells

Figure 3A:
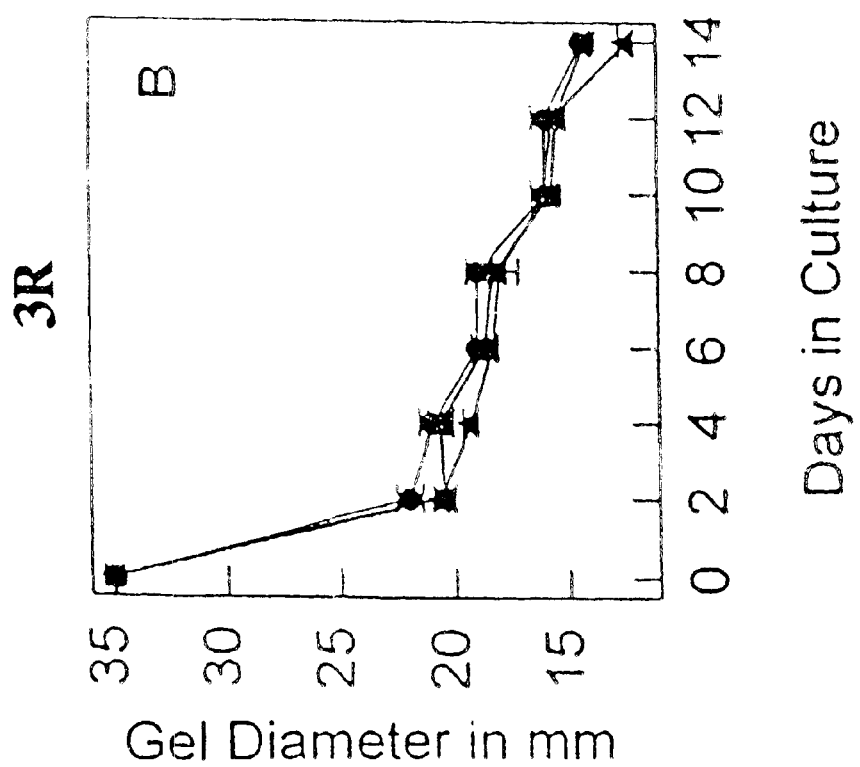
FIGS. 3A and 3B. Contraction of type I collagen gels was compared for papillary dermal fibroblasts (A) and reticular dermal fibrobiasts (B) from the same individual. Cells, 500,000 per 35-mm well, were unlabelled (●), DiI-labelled (▲), or DiO-labelled (■), ± standard deviation of the mean.
Figure 3B:
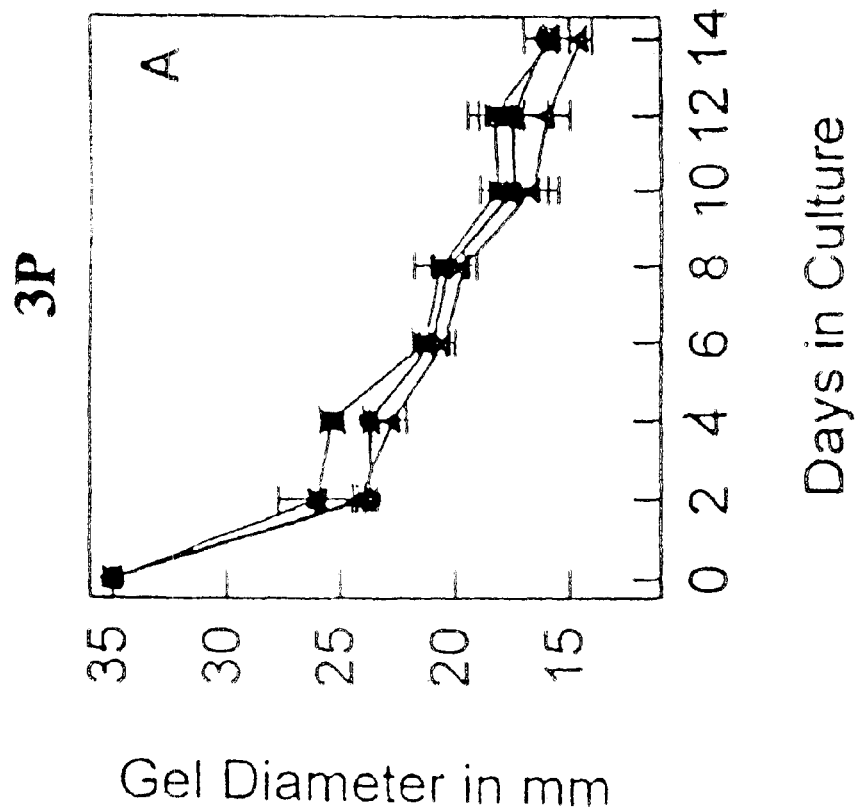

Dermal fibroblasts, when incorporated within free-floating type I collagen gels, induce contraction of the gel. (56–59, 66, 67, 74) Contraction occurs ion an initial rapid phase that lasts for about 48 hours followed by a prolonged phase of slower contraction. The rate of contraction during the first 48 hours has been shown to be a useful discriminator for papillary and reticular dermal cells. (66) As expected, equivalent numbers of reticular dermal cells contracted gels at a faster initial rate than did papillary dermal cells (FIG. 3). Labelling with DiI and with DiO, under the conditions reported here, did not alter the ability of either type of dermal cells to contract the gels (FIGS. 3A and 3B). The data for the unlabelled and dye-labelled cells were compared using the paired t-test and were found not to be statistically significant at the 95% confidence level. However, cells labelled with higher concentrations of the dyes contracted the gels at significantly reduced rates (data not shown).

Identifying Papillary and Reticular Dermal Cells in Mixed and Bilayered Gels

Dermal and skin equivalents were prepared that contain papillary and reticular dermal fibroblasts in their native configurations, that is in a bilayer. Collagen gels containing equal numbers of papillary and reticular dermnal cells were seeded into type I collagen gels either as random mixtures or as defined layers. The studies described below were performed using DiI-labelled papillary cells and DiO-labelled reticular cells in order to identify specific cell types once they had been seeded into collagen gels.

Figure 4:
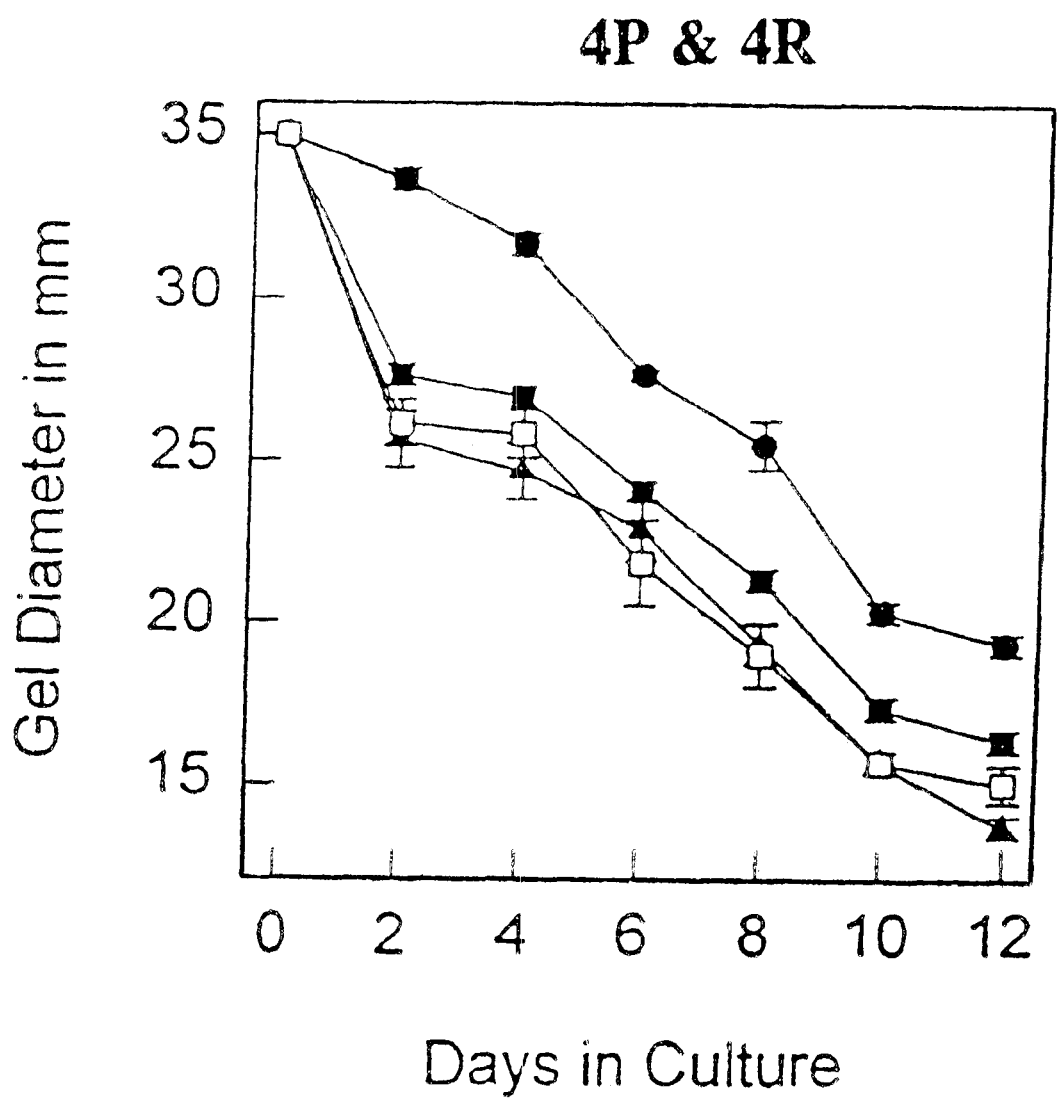
FIG. 4. Contraction of type I collagen gels was compared for DiI-labelled papillary dermal cells alone (●), DiO-labelled reticular dermal fibroblasts alone (▲), equal numbers of randomly mixed DiI-labelled papillary and DiO-labelled reticular dermal cells (■), and bilayered gels containing equal numbers of DiI-labelled papillary and DiO-labelled reticular dermal cells (□). Each 35-mm well contained a total of 250,000 cells, ±standard deviation of the mean.

As shown in FIG. 4, the initial rate of gel contraction was different from that shown in FIGS. 3A and 3B because these gels contained half the number of cells. However, papillary and reticular dermal cells maintained their respective abilities to contract the gels at different rates. Labelling with DiI or with DiO did not interfere with gel contraction. Gels that contained randomly mixed papillary and reticular dermal cells contracted gels at a rate intermediate to that of papillary and reticular cells alone. The data for the layered gels were compared with that for the other gels and was found to be statistically significant at the 95% confidence level. Bilayered gels containing papillary and reticular cells contracted at the same rate as did gels that contained only reticular cells. Furthermore, these gels contracted as a single entity, which indicates the fusion of the two layers.

Figure 6:
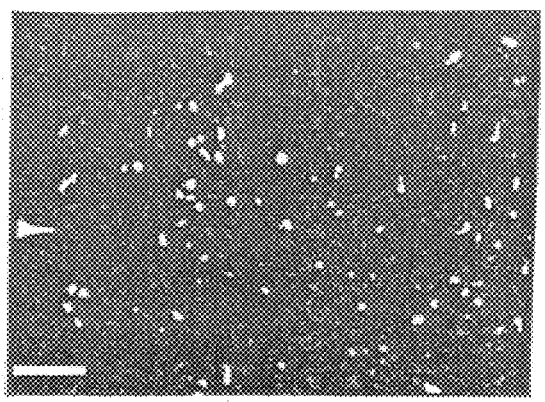
FIG. 6. DiO-labelled reticular dermal were seeded into a type I collagen gel which was cultured for 14 days. Cross-section of the gel reveals that fewer cells have migrated to the gel surface (arrowhead) than that shown in FIG. 5. Magnification, 155×; 1 cm=65 µm.
Figure 7A:
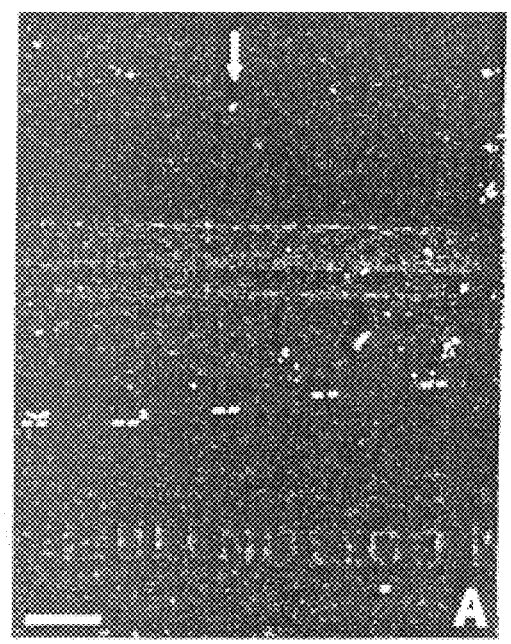
FIGS. 7A and 7B. DiI-labelled papillary dermal cells (A) and DiO-labelled reticular cells (B) were seeded into separate layers of type I collagen to form a bilayered gel which was cultured for 28 days. Cross-section of the gel was photographed in overlapping fields in order to present the entire thickness of the gel. The field shown in panel A was photographed using a rhodamine filter and the field shown in panel B was photographed using a fluorescein filter. The upper surface of the gel is indicated with an arrow and the lower surface is indicated with an arrowhead. The intensity of the DiI label was considerably less than that in FIG. 1. Consequently, DiI-labelled cells cannot be seen with the fluorescein filter in place. Note that papillary cells in panel A and reticular cells in panel B remain in their respective layers. Dashed lines indicate the boundaries between the top and bottom portions of the gel. Magnification, 130×; 1 cm=77 μm.
Figure 7B:
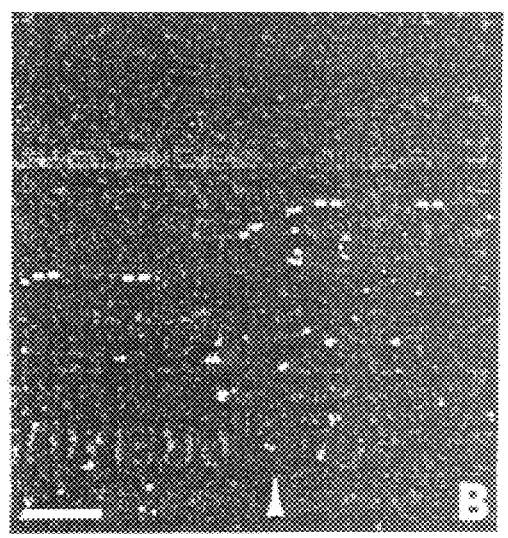

Following the contraction study, the gels were fixed and frozen sections were cut for histologic examination. Some of the gels remained in culture for up to 5 weeks. Examples of contracted gels cultured for 2 weeks which contain DiI-labelled papillary dermal cells and DiI-labelled reticular cells are shown in FIGS. 5A and 5B, respectively. In both cases, cells have migrated to the surfaces of these gels to form a cellular capsule. However, fewer DiO-labelled cells migrate to gel surfaces (FIG. 6). Those gels which were seeded with randomly mixed populations of papillary (DiI-labelled) and reticular (DiO-labelled) dermal cells retained this random organization for at least 5 five weeks. However, very few, less than 10%, of the cells that migrated to the surfaces of these gels were reticular dermal cells. Layered gels fused to form a single gel. Although migration of papillary cells and, to a lesser extent, reticular cells to gel surfaces was observed, there was no migration of these cells into the apposing layer (FIGS 7A and 7B).

Discussion

The dermis of adult skin contains two distinctive and functional layers, the papillary and reticular dermis, each of which contains intrinsically different populations of cells. (65, 66) Papillary dermal cells occupy the upper portion of the dermis and provide support and sustenance for the overlying epidermis, while the underlying reticular cells elaborate an extensive collagenous matrix characteristic of the deeper dermis. (62) Techniques exist for obtaining highly enriched populations of either papillary or reticular dermal cells. (65, 66) In vitro studies indicate that papillary and reticular dermal cells differ in their morphologies in monolayer culture, growth kinetics, and abilities to contract type I collagen gels. (65, 66)

The data presented here indicate that human dermal cells can be differentially labelled with vital dyes and, once labelled and embedded in type I collagen gels, such cells retain sufficient amounts of these dyes to be detected for a period of five weeks. These dyes, particularly DiI, did not impair the abilities of these human dermal cells to perform two critical multicomponent and highly coordinated cellular functions, namely cellular proliferation and contraction of type I collagen gels. The inherent differences of papillary and reticular dermal cells to proliferate and to contract gels was unaffected, which indicates that these cells had retained their essential physiologic characteristics. Using prelabelled papillary and reticular dermal cells, it was possible to demonstrate that true bilayered gels had been created. Histologic analysis indicated that the two halves of the gel fused, and this was confirmed by the fact that these bilayered gels contracted as a single entity. Although the two halves of the gel fused, no intermingling of different cell types occurred.

EXAMPLE 5

MSCs for Tissue Regeneration in Deep Wounds

Two types of formulations are described here. The first is a multilayer skin equivalent that takes advantage of the one or more layers of MSC-derived dermal fibroblasts, together with a human keratinocyte layer. The second, an injectable formulation, is a loose collagen gel suspension of MSCs that is, for example, applied to deep wounds below a skin equivalent or other graft, to regenerate the lower reticular layers.

The first improves upon current skin equivalents by providing a more complex, multiple dermal layer to support keratinocyte growth, rather than current fibroblast technology. The advantage of dermal layers over single fibroblastic feeder layers is the potential for improved vascular invasion to the reticular layer, while simultaneously having a superior layer of papillary cells to enhance the keratinocyte proliferation. The availability of early progenitors (MSCs) rather than fully mature dermal fibroblasts provides more rapid integration in the patient.

The MSC-derived dermal cells are grown in submerged collagen gels and co-cultured with keratinocytes. The major parameters varied in the formulations are the type of collagen, the concentration, the exact timing of administering the MSCs to the gel, the state of differentiation of the MSCs when they are placed in the gel and the timing of the placement of the keratinocyte culture. Finally, raising the co-culture to the air-water interface to initiate cornification of the epidermis can be varied. These variables are optimized to generate a working formulation for in vivo studies in wounds in athymic mice. Skin grafts are tested side by side with those supplemented with MSCs in collagen gels without prior differentiation as a control.

Multiple layered grafts are then used in experiments as the in vitro experiments reveal ways to drive MSC towards a reticular versus papillary dermal cell. These latter formulations will consist of two collagen gels, one that has been seeded with MSCs and allowed to differentiate towards a reticular dermal cells, and another seeded separately with MSCs and incubated under conditions that promote papillary dermal cells. The two gels are fused together in culture and allowed to differentially contract prior to implantation. Thicknesses of the layers are optimized.

Modification of injectable formulations of MSCs already in use for other indications provide a loose collagen suspension with varying concentration of collagen and cells in the preparation.

Cited Literature

1. Parenteau, N. L., Nolte, C. M., Bilbo, P., Rosenberg, M., Wilkins, L. M., Johnson, E. M., Watson, S., Mason, V. S., BelL E. Epidemis generated in vitro: practical considerations and applications. *J. Cellular Biochem.* 45:245–251, 1991.
2. Holbrook, K A. Structure and function of the human skin in development. in: *Physiology, Biochemistry, and Molecular Biology of Skin,* 2nd ed. (L A Goldsmith, Ed.) Oxford University Press, Oxford, 1991, pp 63–110.
3. Bayreuther, K, Rodemann, H. P., Francz, P. I., Maier, K Differentiation of fibroblast stem cefis. *J Cell Science* 10 (Suppl.): 115–130, 1988.
4. Fleming, J. E., Jr. Haynesworth, S. E., Baber, M. A., Caplan, A. I. Mesenchymal stem cell epitopes in human skin, in preparation, 1996.
5. Caplan, A. Mesenchymai stem cells. *J Ortho. Res.* 9: 641–650, 1991.
6. Haynesworth, S. E., Baber, M. A., Caplan, A. I. Cell surface antigens on human marrowderived mesenchymal cells are detected by monoclonal antibodies. *Bone* 13: 69–80, 1992.
7. Holbrook, K. A. Minami, S. A. Hair follicle embryogenesis in the human: characterization of events in vivo and in vitro. *Ann. NY Acad, Sci* 642: 167–196, 1991.
8. Connolly, T, Bruder, S, Kerrigan. L. Dexamethasone induces the expression of a type I BMP receptor inpluripotential mesenchymal progenitor cells. *Trans. Orth. Res. Soc.* 21:180, 1996.
9. Rhinewald, J. G., Green, H. Serial cultivation of human epidermal keratinocytes: The formation of keratinizing colonies from single cells. *Cell* 6:331, 1975.
10. Hansbrough, J. F., Morgan, J., Greenleat G., Parikh, M., Nolte, C., Willkins, L. Evaluation of Graftskin composite grafts on full-thickness wounds on athymic mice. *J. Burn Care Rehabil.* 15:346–353, 1994.
11. Lazarus, H. M., Haynesworth, S. E., Gerson, S. L., Rosenthal N. S., Caplan, A. I. Ex vivo expansion and subsequent infusion of human bone marrow-derived stromal progenitor cells (mesenchymal progenitor cells): implications for therapeutic use. *Bone Marraw Transplant.* 16:557–564, 1995.
12. Ariga, T. and Yu, R. K. (1987). Characterization of Sulfated Glucuronic Acid Containg Glycolipids Reacting with IgM-proteins in Patients with Neuropathy. *J. Biological Chemistry.* 262:2. 848–853.
13. Breathnach, A. S. (1978). Development and differentiation of dermal cells in man. *J. Invest. DermatoL* 71:208.
14. Briggaman, R. A. and Wheeler, C. E. (1971). Epidermal-Dermal Interactions in Adult Human Skin. *J. Invest. Derm.* 56(1):18–26.
15. Brighton, C. T. and Woodbury 11. R. A. (1992). The pericyte as a possible osteoblast progenitor cell. *Clinical Orthopaedics.* 275: 287–298.
16. Caplan, A. I (1991). Mesenchymal Stem Cells. *J. Ortho. Res.* 9:641–650.
17. Chou, D. K. and Jungalwal, F. B. (1986). Structure of Sulfated Glucuronyl Glycolipids in the Nervous System Reacting with HNK-1 Antibody and some IgM Paraproteins in Neuropathy. *J. Biological Chemistry.* 261:25. 11717–11725.
18. Coffin, J. D. and Poole, T. J. (1991). Endothelial Cell Origin and Migration in Embryonic Heart and Cranial Blood Vessel Development. *The Anatomical Record.* 231: 383–395.
19. Gilchrest, B. A. and Year, M. (1990). Cellular and Molecular Mechanisms of Cutaneous Aging. *J. Denm. Surg. OncoL* 16)10):915–922.
20. Hall, P. A. and Watt, F. M. (1989). Stem Cells: The Generation and Maintenance of Cellular Diversity. *Development* 106:619–633.
21. Haynesworth, S. E., Baber,M. A., and Capian, A. I. (1992). Cell Surface Antigens on Human Marrow-Derived Mesenchymal Cells are Detected by Monoclonal Antibodies. *Bone* 13:69–80.
22. Haynesworth, S. E., Goshima, I., Goldberg, V. M., and Caplan, A. I. (1992). Characterization of cells with osteogenic potential from human marrow. *Bone* 13:81–88.
23. Holbrook, K. A. Structure and Function of the Developing Human Skin. Chapter 2 In Biochemistry and Physiology of the Skin. 2nd edit. L. A. Goldsmith, Ed. Oxford University Press. New York, N.Y. 1991.
24. Holbrook, K. A. (1979). Human epidermnal embryogenesis. *International J of Dermatology.* Vol 18, No. 5. 329–356.
25. Holbrook, K. A. and Hoff, B. A. (1984). Structure of the Developing Human Embryonic and Fetal Skin. *Seminars in Dermatology.* 3:3. 185–201.
26. Holbrook. K. A. and Smith. L. T. (1981). Ultrastructural aspects of human skin during embryonic, fetal, neonatal and adult periods of life. Morphogenesis and Malformation of the skin. R. J. Blandau (ed). Alan Liss, N.Y., 9–38.
27. Holbrook, K. A. (1989). Developmental landmarks in the ontogeny of human embryonic and fetal skin: Implications for prenatal diagnosis of inherited skin disease. Cutaneous development aging and repair. G. Abatangelo and J. M. Davidson (eds.) Fidia Research series vol. 18. Liviana Press, Padova. p.245–262.
28. Holbrook, K. A. and Minami, S. I-(1991). Hair Follicle Embryogenesis in the Human. The Molecular and Structural Biology of Hair Vol. 642 of the Annals of the New York Academy of Sciences 167–195.

29. Ilyas, A. A. and Quarles, R. H. (1986). Sulfated Glucuronyl Glycolipids Reacting with Anti-Myelin-Associated Glycoprotein Monocional Antibodies Including IgM Paraproteins in Neuropathy: Species Distribution and Partial Characterization of Epitopes. *Brain Research.* 385:1–9.

30. Johnson, C. L. and Holbrook, K. A. (1989). Development of Human Embryonic and Fetal Dermal Vasculature. *J. Investigative Dermatology* 93:1 OS-1 7S.

31. Klagsbrun, M. (1991). Regulators of Angiogenesis. *Annu. Rev. PhysioL* 53:217–239.

32. Kurban, R. S- and Bhawan, J. (1990). Histologic Changes in Skin Associated with Aging. *J Derm. Surg-OncoL* 16)10):908–914.

33. Lapiere, C. M. and Colige, A. (1990). Response to Epidermal Growth Factor of Skin Fibroblasts from Donors of Varying Age is Modulated by the Extracellular Matrix. *J. Cell. Physio-* 145:450–457.

34. Lavker, R. M- and Dong, G- (1986). Morphology of Aged Skin. *Dermnatologic Clinics.* 4(3):379–389.

35. Smith, L. T- and Holbrook, K. A. (1982). Structure of the dermal matrix in the adult during development. *J Invest. Dermatology.* 79:93–104.

36. Smith, L. T- and Holbrook, K. A. (1986). Embryogenesis of the dermis in human skin. *Pediatric dermatology* 3(4):271–280.

37. Lipton, B. H. and Karasek. M. A. (1990). Microvessel endothelial cell transdifferentiation: phenotypic characterization. *Differentiation* 46: 117–133.

38. Morohunfola, Kehind A. (1992). The Differentiation of Skin and its Appendages, Normal Development of Papillary Ridges. *The Anatomical Record.* 232:4. 587.

39. Nehls, V. and Drenckhahn, D. (1993). The versatility of microvascular pericytes: from mesenchyme to smooth muscle? *Histochemistry* 99:1–12.

40. Owen, M. S. (1985). Lineage of Osteogenic Cells and their Relationship to the Stromal System. In: *Bone and Mineral Research.* edited by W. A. Peck. Vol.3 page 1.

41. Noden, D. M. (1990). Origins and Assembly of Avian Embryonic Blood Vessels. Embryonic Origins of Defectice Heart Development Volume 588 of the Annals of the New York Academy of Sciences.

42. Odland, G. F. Structure of the Skin. Chapter 1 In Biochemistry and Physiology of the Skin. 2nd edit. L. A. Goldsmith, Ed. Oxford University Press. New York, N.Y. 1991.

43. Sengel, P. Epidermal-Dermal Interactions During Formation of Skin and Cutaneous Appendages. Chapter 3 In Biochemistry and Physiology of the Skin. 2nd edit. L. A. Goldsmith, Ed. Oxford University Press. New York, N.Y. 1991.

44. Smith, L. T. and Holbrook, K. A- (1986). Embryogenesis of the Dermis in Human Skin. *Pediatric Dermatology-* 3:4. 271–280.

45. Smith, L. T. and Holbrook. K. A. (1982). Development of Dermal Connective Tissue in Human Embrvonic and Fetal Skin. *Scanning Electron Microscopy.* 4:1745–1751.

46. Suter, M. M. (1990). Differential Expression of Cell Surface Antigens of Canine Keratinocytes Defined by Monoclonal Antibodies. *J. of Histochemistry and Cytochemistry.* 38:4. 541–549.

47. Tonnesen, M. G. and Clark, A. F- (1985). Expression of Fibronectin, Lamminin, and Factor VIII-Related Antigen During Development of the Human Cutaneous Microvasculature.

48. Voros, E. and Robert, A. M. (1990). Age Related Changes of the Human Skin Surface. *Gerontology.* 36:276–285.

49. Wessels, N. K. (1965). Morphology and Proliferation during Early Feather Development. Developmental Biology- 12:131 –153.

50. Willen, M. D. and Caplan, A. I. (1991). Patterns of Glycosaminoglycan-Proteoglycan Immunostaining in Human Skin During Aging. *J. Invest. Derm*96 6:968–974.

51. Westgate, G. E., and Couchman, J. R. (1984). Immunohistochemical localization of basement membrane components during hair follicle morphogenesis. *J. Invest. Dermatology-* 94: 259–264.

52. Jahoda, C. and Oliver, R. F. (1984). Induction of hair growth by implantation of cultured dermal papilla cells. *Nature* 311:560–562.

53. Weinberg, W. C. and Lichti, U. (1993). Reconstruction of Hair Follicle Development In Vivo: Determination of Follicle Formation, Hair growth, and Hair Quality by Dermal Cells. *J. Invest. Dermatology* 100: 229–236.

54. Cavallo, T. (1973). Ultrastructural autoradiographic studies of the early vasoproliferative response in tumor angiogenesis. *Am. J. Pathol-* 70: 345–362.

55. Bruder, S. and Caplan, A. I. (1989). First bone formation and the Dissection of an Osteogenic Lineage in the embryonic chick tibia is revealed by monocional antibodies against osteoblasts. 10:359–375.

56. Bell, E., Ehrlich, H. P., Buttle, D., Nakatsuji, T. Living tissue formed in vitro and accepted as a skin-equivalent tissue of full thickness. Science, 211, 1052, 1981.

57. Bell, E., Sher, S., Hull, B., Merrill, C., Rosen, S., Chamson, A., Asselineau, D., Dubertret, L., Coulomb, B., Lapiere, C., Nusgens, B., and Neveux, Y. The reconstitution of living skin. J. Invest. Dennatol. 81, 2s, 1983.

58. Allen, T. D. and Schor. S. L. The contraction of collagen matrices by dermal fibroblasts. J. Ultrastr. Res. 83, 205, 1983.

59. Coulomb, B., Dubetret, L, Bell, E., and Touraine, R. The contractility of fibroblasts in a collagen lattice is reduced by corticosteroids. J. Invest. Dermatol. 82, 341, 1984.

60. Tuan, T-L., Keller, L. C., Sun, D., Ninuii, M. E., and Cheung, D. Dermal fibroblasts activate keratinocyte outgrowth on collagen gels. J. Cell Sci., 107, 2285, 1994.

61. Brown, L. J., Geesin, J. C., Rothnagel, J. A., Roop, D. R., and Gordon, J. S. Retinoic acid suppression of loricrin expression in reconstituted human skin cultured at the liquidair interface. J. Invest. Dennatol. 102, 886, 1994.

62. Stenn, K. S. The skin. In Weiss, L., ed., Histology, Cell and Tissue Biology, 5th ed. New York, Elsevier Biomedical, p. 569.

63. Reynolds, A. J., Oliver, R. F., and Jahoda, C. A. B. Dermal cell populations show variable competence in epidermal cell support: stimulatory effects of hair papilla cells. J. Cell Sci. 98, 75, 1991.

64. Limat, A., Hunziker, T., Waelti, E. R., Inaebnit, S. P., Wiesmann, U., and Braathen, L. R. Soluble factors from human hair papilla cells and dermal fibroblasts dramatically increase the clorial growth of outer root sheath cells. Arch. Dermatol. 285, 205, 1993.

65. Harper, R. A. and Grove, G. Human skin fibroblasts derived from papillary and reticular dermis: differences in growth poteiltial in vitro. Science 204, 526, 1979.

66. Schafer, I. A., Pandy, M., Ferguson, R., and Davis, B. R. Comparative observation of fibroblasts derived from the papillary and reticular dermis of infants and adults: growth kinetics, packing density at confluence and surface morphology. Mech. Ageing Devel. 31, 275, 1985.

67. Andujar, M. B., Melin, M., Guerret, S., and Grimaud, J. A. Cell migration influences collagen gel contraction. J. Submicroso. Cytol. Pathol. 24, 145, 1992.

68. Honig, M. G. and Hume, R. I. DiI and DiO: versatile fluorescent dyes for neuronal labelling and pathway tracing. Trends Neural Sci. 12, 333, 1989.
69. Westergren-Thorsson, G., Onnervik, P-O., Fransson, L-A., and Maimstrom, A. Proliferation of cultured fibroblasts is inhibited by L-iduronate-containing glycosaminoglycans. J. Cell. Physiol. 147, 523, 1991.
70. Lennon, D. P., Haynesworth, S. E., Young, R. G., Dennis, J. E., and Caplan, A. I. A chemically defined medium supports in wtro proliferation and maintains the osteochondral potential of rat marrow-derived mesenchymal stem cells. Exp. Cell Res. 219, 211, 1995.
71. von Bartheld, C. S., Cunningham, D. E., and Rubel, E. W. Neuronal tracing with DiI: decalcification, cryosectioning, and photoconversion for light and electron microscopic analysis. J. Histochem. Cytochem. 38, 725, 1990.
72. Johnson, G. D., Davidson, R. S., McNamee, K. C., Russell, G., Goodwin, D., and Holborow, E. J. Fading of immunofluorescence during microscopy: a study of the phenomenon and its remedy. J. Immunol. Methods 55, 231, 1982.
73. Kono, T., Tanh, T., Furukawa, M., Mizuno, N., Kitajima, J., Ishii, M., Hamada, T., and Yoshizato, K. Cell cycle analysis of human dermal fibroblasts cultured on or in hydrated type I collagen latices. Arch. Dennatol. Res. 282, 258, 1990.
74. Grinnell, F. and Nakagawa, S. Spatial regulation of fibroblast proliferation: an explanation for cell regression at the end of the wound repair. Prog. Clin. Biol. Res. 365, 155, 1991.
75. Nishiyama, T., Tsunenaga, M., Nakayama, Y., Adachi, E., and Hayashi T. Growth rate of human fibroblasts is repressed by the culture within reconstituted collagen matrix but not by the culture on the matrix. Matrix 9, 193, 1989.
76. Serbedzija, G. N., Fraser, S. E., and Bronner-Fraser, M. Pathways of trunk neural crest cell migration in the mouse embryo as revealed by vital dye labelling. Development, 108, 605, 1990.
77. Stem, C. The marginal zone and its contribution to the hypoblast and primitive streak of the chick embryo. Development, 109, 667, 1990.
78. 1 Ledley, F. D., Soriano, H. E., O'Malley, B. W., Lewis, D., Darlington, G. J., and Finegold, M. DiI as a marker for cellular transplantation into solid organs. Biotechnique 13, 580, 1992.
79. Horne, K. A., Jahoda, C. A. B., and Oliver, R. F. Whisker growth induced by implantation of cultured vibrissa dermal papilla cells in the adult rat. J. Embryol. Exp. Morphol. 97, 111, 1986.
80. Weinberg, W. C., Goodman, L. V., George, C., Morgan, D. L., Ledbetter, S., Yuspa, S. H., and Lichti, U. Reconstitution of hair follicle development in vivo: determination of follicle formation, hair growth, and hair quality by dermal cells. J. Invest. Dermatol. 100, 229, 1993.
81. Yaeger, P. C., Stiles, C. D., and Rollins, B. J. Human keratinocyte growth-promoting activity on the surfaces of fibroblasts. J. Cell. Physiol. 149, 110, 1991.

What is claimed is:

1. A multilayer skin equivalent consisting essentially of:
   (i) a scaffold layer incorporated with dermis-forming cells consisting essentially of mesenchymal stem cells and
   (ii) a keratinocyte layer.

2. The multilayer skin equivalent of claim 1 wherein the mesenchymal stem cells are human.

3. The multilayer skin equivalent of claim 1, wherein the mesenchymal stem cells are autologous.

4. The multilayer skin equivalent of claim 1 wherein the scaffold layer contains at least one extracellular matrix component.

5. The multilayer skin equivalent of claim 4 wherein the extracellular matrix component is selected from the group consisting of collagen, elastin, intercellular adhesion molecules, neural cell adhesion molecule, laminin, heparin binding growth factors, fibronectin, proteoglycans, tenascin, E-cahedrin, and fibrillin.

6. The multilayer skin equivalent of claim 1 wherein the mesenchymal stem cells are proliferated and further differentiated on the scaffold layer.

7. The multilayer skin equivalent of claim 1 wherein at least one of said layers further includes at least one pharmaceutical agent which promotes adhesion or angiogenesis of the skin equivalent.

8. The multilayer skin equivalent of claim 1 wherein the keratinocytes are obtained from an individual to be treated with the multilayer skin equivalent.

9. The multilayer skin equivalent of claim 1 wherein the keratinocytes are proliferated on the scaffold layer.

10. The multilayer skin equivalent of claim 1 wherein the keratinocytes are proliferated on the scaffold layer in Rheinwald Green medium.

11. A multilayer dermal equivalent consisting essentially of at least one dermis-forming layer consisting essentially of mesenchymal stem cells and a layer selected from the group consisting of
    (i) a layer of at least one extracellular matrix component containing papillary dermis forming cells; and
    (ii) a layer of at least one extracellular matrix component containing reticular dermis forming cells.

12. The multilayer dermal equivalent of claim 11 wherein at least two layers are in laminar relationship.

13. The multilayer dermal equivalent of claim 11 wherein the extracellular matrix component is selected from the group consisting of collagen, elastin, intercellular adhesion molecules, neural cell adhesion molecule, laminin, heparin binding growth factors, fibronectin, proteoglycans, tenascin, E-cahedrin, and fibrillin.

14. The multilayer dermal equivalent of claim 11 further comprising a keratinocyte layer.

15. The multilayer dermal equivalent of claim 11 wherein at least one of said layers further includes a bioactive factor which enhances proliferation, commitment or differentiation of mesenchymal stem cells into dermal components, either in vitro or in vivo.

16. The multilayer dermal equivalent of claim 11 wherein at least one of said layers further includes at least one pharmaceutical agent which promotes adhesion or angiogenesis of the dermal skin equivalent.

17. The multilayer dermal equivalent of claim 11 wherein the papillary and reticular dermis forming cells are from the same individual.

18. The multilayer dermal equivalent of claim 11 wherein the papillary and reticular dermis forming cells are from an individual to whom the multilayer dermal equivalent is to be administered.

* * * * *